US012691058B2

(12) United States Patent (10) Patent No.: US 12,691,058 B2
Kole et al. (45) Date of Patent: Jul. 28, 2026

(54) SUBLINGUAL OR BUCCAL DOSAGE FORMS COMPRISING ANTIOXIDANTS FOR TREATMENT OF CENTRAL NERVOUS SYSTEM DISORDERS

(71) Applicant: Beyond Barriers Therapeutics, Inc., Glencoe, IL (US)

(72) Inventors: Ryan Kole, Glencoe, IL (US); John Marshall, Glencoe, IL (US); Charles Polsky, Glencoe, IL (US); Brian Reinhardt, Glencoe, IL (US); Thomas A. DeGregoris, Glencoe, IL (US)

(73) Assignee: Beyond Barriers Therapeutics, Inc., Glencoe, IL (US)

( * ) Notice: Subject to any disclaimer, the term of this patent is extended or adjusted under 35 U.S.C. 154(b) by 0 days.

(21) Appl. No.: 19/358,262

(22) Filed: Oct. 14, 2025

(65) Prior Publication Data

US 2026/0151332 A1     Jun. 4, 2026

Related U.S. Application Data

(63) Continuation of application No. PCT/US2024/058158, filed on Dec. 2, 2024.

(60) Provisional application No. 63/604,873, filed on Nov. 30, 2023.

(51) Int. Cl.
| | |
|---|---|
| *A61K 9/00* | (2006.01) |
| *A61K 31/198* | (2006.01) |
| *A61K 47/10* | (2017.01) |
| *A61K 47/12* | (2006.01) |
| *A61K 47/14* | (2017.01) |
| *A61K 47/18* | (2017.01) |
| *A61K 47/20* | (2006.01) |
| *A61K 47/22* | (2006.01) |
| *A61K 47/26* | (2006.01) |
| *A61K 47/32* | (2006.01) |
| *A61K 47/38* | (2006.01) |
| *A61K 47/40* | (2006.01) |
| *A61K 47/42* | (2017.01) |

(52) U.S. Cl.
CPC ............ *A61K 9/006* (2013.01); *A61K 9/0056* (2013.01); *A61K 31/198* (2013.01); *A61K 47/10* (2013.01); *A61K 47/12* (2013.01); *A61K 47/14* (2013.01); *A61K 47/183* (2013.01); *A61K 47/20* (2013.01); *A61K 47/22* (2013.01); *A61K 47/26* (2013.01); *A61K 47/32* (2013.01); *A61K 47/38* (2013.01); *A61K 47/40* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 10,213,474 B2 | 2/2019 | Uchegbu et al. | |
| 11,612,642 B2 | 3/2023 | Kole et al. | |
| 12,257,292 B2 | 3/2025 | Kole et al. | |
| 2002/0198161 A1 | 12/2002 | Brash et al. | |
| 2006/0099244 A1 | 5/2006 | Guilford | |
| 2011/0111011 A1 | 5/2011 | Giovinazzo et al. | |
| 2013/0059854 A1 | 3/2013 | Ryoo et al. | |
| 2018/0344678 A1 | 12/2018 | Ratan et al. | |
| 2019/0174812 A1 | 6/2019 | Nielsen et al. | |
| 2020/0163874 A1 * | 5/2020 | Chen ................... | A61K 36/185 |
| 2020/0347153 A1 * | 11/2020 | McGowan ............. | A61K 8/675 |
| 2022/0087938 A1 | 3/2022 | Sävmarker et al. | |
| 2022/0143129 A1 | 5/2022 | Arnold et al. | |
| 2022/0257690 A1 | 8/2022 | Czap | |
| 2022/0347095 A1 | 11/2022 | Lim et al. | |
| 2023/0263725 A1 | 8/2023 | Kole et al. | |
| 2025/0152536 A1 | 5/2025 | Kole et al. | |
| 2025/0213661 A1 | 7/2025 | Kole et al. | |

OTHER PUBLICATIONS

Andrews, et al., "Bitter-blockers as a taste masking strategy: A systematic review towards their utility in pharmaceuticals", European Journal of Pharmaceutics and Biopharmaceutics, 2021, 158:35-51.

Castile, et al., "Development of in vitro models to demonstrate the ability of PecSys®, an in situ nasal gelling technology, to reduce nasal run-off and drip", Drug Development and Industrial Pharmacy, 2013; 39(5): 816-824, Informa Healthcare USA, Inc., ISSN 0363-9045 print/ISSN 1520-5762 online DOI: 10.3109/03639045. 2012.707210, 2013.

Chiew, et al., "Interventions for paracetamol (acetaminophen) overdose", Cochrane Database of Systematic Reviews, Issue 2, Art. No. CD003328 DOI: 10.1002/14651858.CD003328.pub3, Feb. 23, 2018.

Eakin, et al., "Efficacy of N-Acetyl Cysteine in Traumatic Brain Injury", PLoS ONE, vol. 9, No. 4, Article No. e90617 doi:10.1371/journal.pone.0090617, 2014.

Fisher, et al., "Police Officers Can Safely and Effectively Administer Intranasal Naloxone", Prehospital Emergency Care, Nov.-Dec. 2016 20(6):675-680.

Hoffer, et al., "Amelioration of acute sequelae of blast induced mild traumatic brain injury by N-acetyl cysteine: a double-blind, placebo controlled study", PLoS One. 2013;8(1):e54163.

Nichol, et al., "Erythropoietin in traumatic brain injury (EPO-TBI): a double-blind randomised controlled trial", The Lancet, vol. 386, No. 10012, p. 2499-2506 (2015).

Ouyang, et al., "Successful bystander-administered intranasal naloxone reversal of opioid overdose between two veterans: A case report", Ment Health Clin [Internet], vol. 7, No. 6, 2017, pp. 287-289.

Rabinowicz, et al., "Improvement of Intranasal Drug Delivery with Intravail® Alkylsaccharide Excipient as a Mucosal Absorption Enhancer Aiding in the Treatment of Conditions of the Central Nervous System", Drugs in R&D (2021) 21:361-369; https://doi.org/10.1007/s40268-021-00360-5.

(Continued)

*Primary Examiner* — Dominic Lazaro
(74) *Attorney, Agent, or Firm* — Neal, Gerber & Eisenberg LLP

(57) ABSTRACT

Sublingual or buccal dosage forms comprise at least one antioxidant compound, such as N-acetyl cysteine (NAC), or a pharmaceutically acceptable salt thereof. The sublingual or buccal dosage forms are administered for treating central nervous system (CNS) disorders, such as traumatic brain injury or stroke.

20 Claims, 5 Drawing Sheets

(56)           References Cited

OTHER PUBLICATIONS

Raeisi, et al., "Commercial hydrogel product for drug delivery based on route of administration", Front. Chem., 12:1336717, doi:10.3389/fchem.2024.1336717, 2024.

Rai, Vineya, "Effects of immunonutrition on biomarkers in traumatic brain injury patients in Malaysia: a prospective randomized controlled trial", BMC Anesthesiol. 17:81 DOI 10.1186/s12871-017-0369-4, 2017.

Senol, et al., "N-Acetylcysteine and Selenium Modulate Oxidative Stress, Antioxidant Vitamin and Cytokine Values in Traumatic Brain Injury-Induced Rats", Neurochemical Research, vol. 39, 2014, pp. 685-692.

Zhou, et al., "Intravenous Administration of Stable-Labeled N-Acetylcysteine Demonstrates an Indirect Mechanism for Boosting Glutathione and Improving Redox Status", wileyonlinelibrary.com, 2015.

* cited by examiner

SUBLINGUAL OR BUCCAL DOSAGE FORMS COMPRISING ANTIOXIDANTS FOR TREATMENT OF CENTRAL NERVOUS SYSTEM DISORDERS

CROSS-REFERENCE TO RELATED APPLICATIONS

This application is a continuation of International Application No. PCT/US2024/058158, filed Dec. 2, 2024, which claims the benefit of U.S. Provisional Application No. 63/604,873, filed Nov. 30, 2023, the contents of which are incorporated by reference in their entirety.

FIELD OF THE INVENTION

The present disclosure is directed to sublingual or buccal dosage forms, methods, and kits for treatment of central nervous system (CNS) disorders.

BACKGROUND

Central nervous system (CNS) disorders are a collection of neurological diseases having various underlying causes, including trauma, degeneration, infection, and autoimmune disease. Oxidative stress resulting from high levels of reactive oxygen and reactive nitrogen species (ROS/RNS) can play a key role in the progression of many central nervous system disorders such as traumatic brain injury (TBI), Alzheimer's disease, and Parkinson's disease. For traumatic brain injury disorders, damage from the injury is generally divided into primary injuries, a direct result of the impact itself, and secondary injuries, biochemical and cellular events that occur over the ensuing hours and days and exacerbate the initial insult. While the exact mechanisms of this secondary injury are complex, substantial previous work has shown that oxidative stress, resulting from high levels of reactive oxygen species and reactive nitrogen species (ROS/RNS), plays a key role in pathology developing during the period of secondary injury. As a result, a number of research studies have focused on the use of antioxidants as therapeutic agents to reduce ROS/RNS species. Preclinical studies across disparate animal models have had some success in using antioxidant therapies for central nervous system disorders such as traumatic brain injury.

Traumatic brain injury is widely recognized as a public health issue for which there is no current effective pharmaceutical therapy. Statistics from the Centers for Disease Control (CDC) show that 2.5 million emergency room visits a year are due to traumatic brain injury. However, in spite of widespread interest, investment and a number of promising preclinical and initial clinical stage studies, every pharmacological agent that has advanced to phase III clinical trials for traumatic brain injury has failed. For instance, despite more than 20 preclinical studies showing that erythropoietin improves outcome following traumatic brain injury, in at least one large multi-center randomized controlled trial, erythropoietin did not reduce the number of patients with severe neurological dysfunction (GOS-E level 1-4) or increase the incidence of deep venous thrombosis of the lower limbs. Nichol et al., "Erythropoietin in traumatic brain injury (EPO-TBI): a double-blind randomised controlled trial", The Lancet, Vol. 386, No. 10012, p 2499-2506 (2015). A clinical study conducted on 81 active duty service members was said to demonstrate that orally administered N-acetylcysteine (NAC) had beneficial effects on the severity and resolution of sequelae of blast induced mild traumatic brain injury. Hoffer et al., "Amelioration of acute sequelae of blast induced mild traumatic brain injury by N-acetyl cysteine: a double-blind, placebo controlled study", PLOS One. 2013; 8(1): e54163.

NAC has been approved by the Food and Drug Administration for other indications. For example, Mucomyst (acetylcysteine solution, USP) was approved as adjuvant therapy for patients with abnormal, viscid, or inspissated mucous secretions in various conditions. Acetadote (acetylcysteine) injection for intravenous use and Cetylev (acetylcysteine) effervescent tablets for oral solution have been approved for acetaminophen overdose to prevent or lessen hepatic injury.

Glutathione is a primary endogenous antioxidant and interventions to increase glutathione concentration are thought to be effective in reducing TBI sequelae. Rai et al., BMC Anesthesiol. 2017 Jun. 15; 17(1): 81. Orally administered NAC, a glutathione precursor, has been shown to be effective in reducing the symptoms of mild-moderate traumatic brain injury in human patients. Hoffer et al., PLOS One. 2013; 8(1): e54163. Cysteine is the rate limiting substrate for endogenous glutathione synthesis. NAC can be directly metabolized to cysteine, or may increase cysteine levels indirectly. However, NAC is subject to extensive first pass intestinal and hepatic metabolism, and therefore has a low bioavailability following oral administration, between 6-10%. Orally administered NAC also may cause nausea, vomiting and diarrhea, exacerbating the symptoms from a TBI making it unlikely that a patient will finish a medication if it is required to be taken for 7 days for example. See Chiew et al., Cochrane Database Syst Rev. 2018 February; 2018(2). Oral delivery is also not a viable administration method for all patients, for example for a person who is unresponsive, not being capable of swallowing a pill, a young child, the elderly, or person with cognitive or motor deficits not capable of swallowing a pill. Ouyang et al., Ment Health Clin. 2018 Mar. 23; 7(6): 287-289; Fisher et al., Prehosp Emerg Care. 2016 November-December; 20(6): 675-680. Additionally, studies have shown oral NAC having a low blood brain barrier permeability. This in combination with the low oral bioavailability, means that following oral administration, very little NAC would be expected to reach the brain. Senol et al., Neurochem Res (2014) 39(4): 685-92. Interestingly the example study in this application did not detect an increase in the concentration of isotope labeled NAC in brain tissue following administration, further highlighting the low blood brain barrier permeability of NAC and suggesting challenges with the oral route of administration. NAC may also be converted to cysteine in peripheral circulation and cysteine itself may be taken up across the blood brain barrier to subsequently increase GSH levels. See Eakin et al., PLOS One. 2014; 9(4): e90617; Zhou et al., J Pharm Sci. 2015 August; 104(8): 2619-26.

Developing non-parenteral formulation can be challenging due to the presence of a thiol (sulfhydryl, —SH) group, which gives NAC a characteristic strong, unpleasant odor.

U.S. Pat. No. 11,612,642 (Beyond Barriers Therapeutics, Inc.) discloses methods and forms for treating central nervous system (CNS) disorders by intranasal delivery of at least one antioxidant compound (such as NAC), allowing for effective treatment of a central nervous system disorder such as traumatic brain injury or stroke.

SUMMARY OF THE INVENTION

In an embodiment, the present disclosure provides a method of treating a central nervous system (CNS) disorder.

The method comprises sublingual or buccal administration to a subject an effective amount of at least one antioxidant compound or a pharmaceutically acceptable salt thereof.

In another embodiment, the present disclosure provides a sublingual or buccal dosage form comprising at least one antioxidant compound or a pharmaceutically acceptable salt thereof. In some embodiments, the at least one antioxidant compound or salt thereof is the only active agent in the dosage form.

In another embodiment, the present disclosure provides a kit for treating a subject having a central nervous system (CNS) disorder. The kit comprises (a) a sublingual or buccal dosage form comprising at least one antioxidant compound or a pharmaceutically acceptable salt thereof, and (b) an intranasal dosage form comprising at least one antioxidant compound or a pharmaceutically acceptable salt thereof. Kit components (a) and (b) may comprise the same antioxidant compound, or they may comprise different antioxidant compounds.

These and other features and advantages of the present sublingual or buccal dosage forms and methods will be apparent from the following detailed description, in conjunction with the appended claims.

DEFINED TERMINOLOGY

Figure 1:
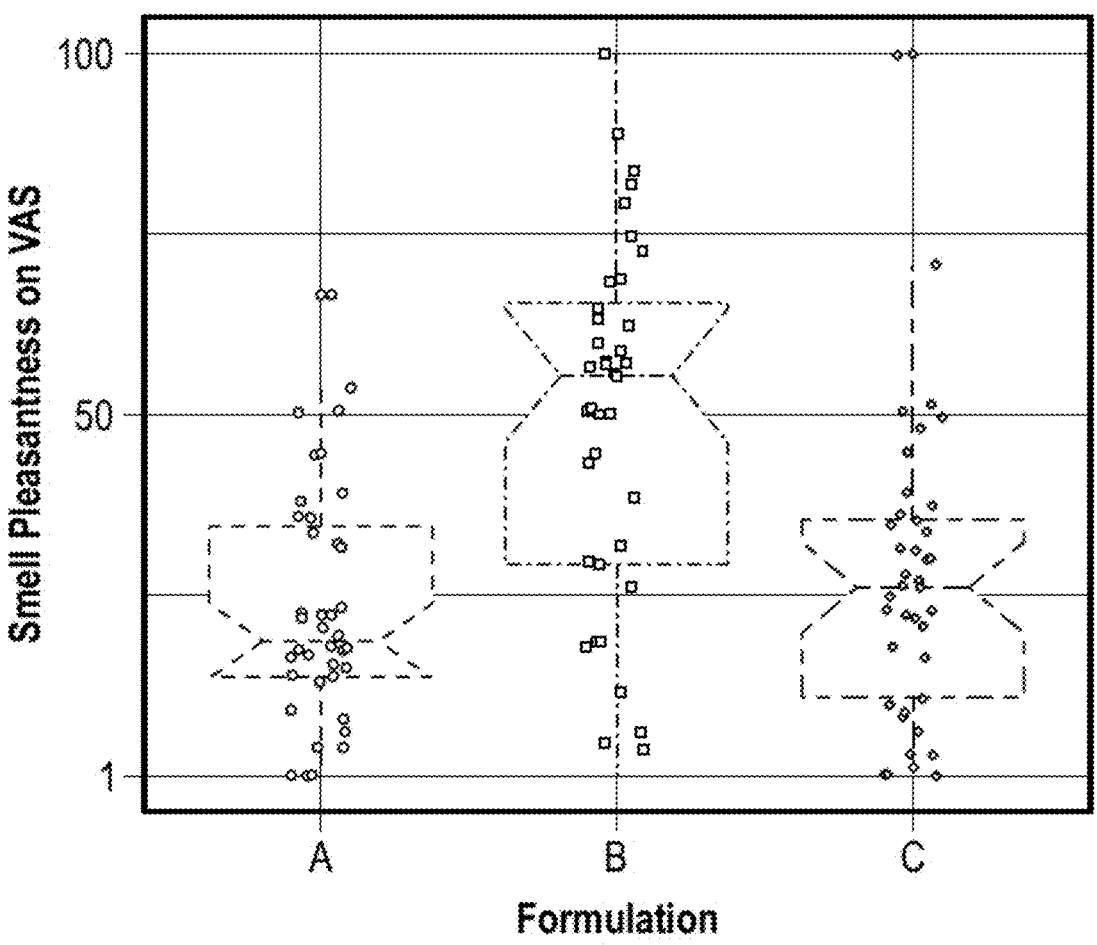
FIG. 1 illustrates some of the results of a sensory smell study of NAC formulations described in Example 5.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

The terms "sublingual administration" and "sublingual or buccal dosage form", as used herein, refer to a pharmaceutical compound or pharmaceutically acceptable salt thereof placed beneath the tongue of a subject (or on the tongue in some circumstances) so that the compound or salt thereof passes through the mucosa of the oral cavity. A sublingual form is placed beneath or on the tongue where it dissolves in the saliva to release the drug in close proximity to the capillary bed of the oral mucosa for transmucosal absorption.

The terms "buccal administration" and "buccal dosage form", as used herein, refer to a pharmaceutical compound or pharmaceutically acceptable salt thereof placed between the gum and the cheek of a subject so that the compound or salt thereof passes through the mucosa of the oral cavity. A buccal dosage form is placed in the buccal cavity between the gum and the cheek, where it dissolves in the subject's saliva, releasing the medicament into the buccal cavity in close proximity to the capillary bed of the oral mucosa.

The terms "oral administration" and "oral dosage form", as used herein, refer to a pharmaceutical compound or pharmaceutically acceptable salt thereof that is ingested or swallowed by a subject so that it passes to the subject's gastrointestinal tract. Oral administration, as used herein, excludes sublingual or buccal administration; likewise, sublingual and buccal dosage forms, as used herein, do not encompass oral dosage forms.

The terms "treat", "treating", and "treatment" refer to a method of alleviating or abrogating a condition, disorder, or disease and/or the attendant symptoms thereof.

The term "effective amount" or "therapeutically effective amount" means a sufficient amount of the compound to treat or ameliorate a condition, disorder, or disease. When used in a medical treatment, an effective amount of one of the present compounds can be employed in pure form or, where such forms exist, in a pharmaceutically acceptable salt. Alternatively, the compound can be administered as a pharmaceutical formulation containing the compound of interest in combination with one or more pharmaceutically acceptable carriers.

The term "subject" includes humans and other primates as well as domesticated and semi-domesticated animals including, but not limited to, poultry, honeybees, cows, sheep, goats, pigs, horses, dogs, cats, rabbits, rats, mice, and the like.

The term "co-administration", as used herein, encompasses administration of two or more agents to a subject so that both agents and/or their metabolites are present in the subject at the same time. Co-administration includes simultaneous administration in separate dosage forms, administration at different times in separate dosage forms, or administration in a dosage form in which both agents are present.

The term "delivery agent" refers to a moiety capable of enhancing the delivery of a pharmaceutical drug to the central nervous system of a subject. Delivery of a pharmaceutical drug may be enhanced by various mechanisms including an increase in transport, diffusion, or stability of the pharmaceutical drug. In some embodiments, the delivery agent increases transport of an antioxidant compound from the oral cavity through the mucosal tissue to the central nervous system.

As used in the specification and appended claims, and in addition to their ordinary meanings, the terms "substantial" or "substantially" mean to within acceptable limits or degree to one having ordinary skill in the art. For example, "substantially cancelled" means that one skilled in the art considers the cancellation to be acceptable.

As used in the specification and the appended claims and in addition to its ordinary meaning, the terms "approximately" and "about" mean to within an acceptable limit or amount to one having ordinary skill in the art. The term "about" generally refers to plus or minus 15% of the indicated number. For example, "about 10" may indicate a range of 8.5 to 11.5. For example, "approximately the same" means that one of ordinary skill in the art considers the items being compared to be the same. It should be understood that any of the values disclosed herein are also a disclosure of the approximate value (e.g., the disclosure of "0.10" shall also constitute a disclosure of "about 0.10"), and any disclosure of an approximate value is a disclosure of the value itself (e.g., the disclosure of "about 0.10" shall also constitute a disclosure of "0.10"), unless the context indicates otherwise.

Unless defined otherwise, all technical and scientific terms used herein have the same meaning as commonly understood by those working in the fields to which this disclosure pertain.

DETAILED DESCRIPTION

The present disclosure generally relates to formulations and methods for treatment of central nervous system (CNS)

disorders that enhance the delivery of antioxidant compounds to the central nervous system. A major barrier to pharmacological treatment of brain disorders is the blood brain barrier, a network of endothelial cells coupled by tight junctions that govern solution flow and movement of compounds in and out of the brain parenchyma and that consequently reduces the effective concentration of a systemically administered compound able to reach the brain. A major barrier to the use of N-acetylcysteine (NAC) for treatment of CNS disorders by oral administration is that it undergoes significant first pass metabolism. Treatment of central nervous system disorders such as traumatic brain injury (TBI) may be enhanced using sublingual or buccal administration of pharmaceutical compounds, resulting in efficient brain delivery of the antioxidant compound. For example, pairing an antioxidant such as N-acetylcysteine (NAC) with sublingual or buccal administration may result in effective delivery of the antioxidant compound to the brain. Buccal or sublingual route of administration for NAC leads to a substantially greater increase in GSH levels, as this route of administration leads to an increased concentration of NAC in peripheral circulation. Metabolism of NAC to cysteine can be followed by cysteine uptake across the blood brain barrier, or some amount of NAC itself may cross the blood brain barrier.

Unlike oral administration, buccal or sublingual administration avoids first pass metabolism. This is well-established aspect of oral administration of active agents, and therefore sublingual or buccal administration will provide better bioavailability of NAC than oral administration. In addition, since high levels of orally dosed NAC has been associated with GI side effects like nausea and vomiting, buccal or sublingual dosing may avoid these undesirable attributes. Additionally, since intranasal dosing may have a strong sulfur smell, some subjects will prefer a dosage form that is not aerosolized, especially for chronic dosing.

The antioxidant compound or pharmaceutically acceptable salt thereof in the sublingual or buccal dosage forms enters the blood in the capillary bed by diffusion through the mucosa of the oral cavity, and is distributed in the bloodstream to the rest of the body. The rate at which the pharmaceutical compound or salt thereof is supplied to the body depends upon, among other things, the rate at which the dosage form dissolves in the mouth. The physical properties of the dosage form determine the degree of contact with the mucosal tissues and consequently the efficiency of the absorption of the medicament.

In some embodiments, the sublingual or buccal dosage form instantaneously releases an effective amount of at least one pharmaceutical compound or salt thereof into the oral cavity of a subject when placed in the subject's oral cavity. In accordance with aspects of the present disclosure, the sublingual or buccal dosage form begins to release an effective amount of at least one pharmaceutical compound or salt thereof into the systemic circulation of a subject within seconds of placing the sublingual or buccal dosage form in the subject's oral cavity. In some embodiments, the sublingual or buccal dosage form induces a pharmacological effect in a subject within about 1 minute to about 20 minutes of placing the sublingual or buccal dosage form in the subject's oral cavity. In some embodiments, the sublingual or buccal dosage form induces a pharmacological effect in a subject after 20 minutes of placing the sublingual or buccal dosage form in the subject's oral cavity.

In some embodiments, the present methods and sublingual or buccal dosage forms have taste and/or smell properties which lead to longer retention in the mouth of the subject, so as to be retained in the mouth for a desired duration. For example, the dosage form can comprise a bitter-blocker or other masking agent in an amount to alleviate bitter taste while maintaining intensity at a desired level. In some embodiments, a subject retains the sublingual or buccal dosage form in her mouth for a time period sufficient to reach a desired blood level of NAC.

In some embodiments, the present methods and sublingual or buccal dosage forms may increase levels or concentrations of glutathione in a subject's brain in addition to or instead of increasing the level or concentration of a compound in either the brain or vasculature, if that compound is sublingually or buccally administered to the subject. Without wishing to be bound by any particular theory, an administered antioxidant compound such as NAC may undergo conversion to cysteine in the subject's vasculature, followed by cysteine uptake across the blood brain barrier, or NAC itself may cross the blood brain barrier to then be converted to cysteine and increase GSH. In this manner, cysteine required for glutathione synthesis in the brain may be facilitated. In some embodiments, N-acetylcysteine is sublingually or buccally administered to a subject in order to increase a level of glutathione in the subject's brain. It is expected the NAC level from sublingual or buccal administration will be greater than from oral administration because it is absorbed through tissue in the oral cavity and not digested, thereby avoiding metabolic degradation in the gastrointestinal tract. Sublingual or buccal administration is not likely to bypass the blood brain barriers, but a potentially surprising increase in GSH is provided compared to oral, due to avoiding first pass metabolism. Buccal or sublingual administration can also lead to significantly faster time to peak concentration compared to oral administration, important for acute care.

Another advantage of sublingual and buccal administration compared to oral administration or intranasal administration is found with subjects having cognitive dysfunction or difficulty swallowing associated with a CNS disorder. The sublingual or buccal dosage form may be easier and more effective in delivering an antioxidant compound or salt thereof to such subjects, compared to trying to swallow oral dosage forms every day or mastering the coordination to squeeze a nasal inhaler and sniff at the same time. For some patient groups, (such as Alzheimer's disease, Parkinson's disease, frontotemporal dementia, Amyotrophic Lateral Sclerosis (ALS), other neurodegenerative diseases, and other cognitive diseases), sublingual or buccal administration may be the easiest route of administration for the patient.

In an embodiment, the present disclosure provides a method of treating a central nervous system disorder. The method comprises sublingually or buccally administering to a subject an effective amount of at least one antioxidant compound or a pharmaceutically acceptable salt thereof. In some instances, CNS disorders, such as during a traumatic brain injury, the blood brain barrier (BBB) can be compromised, which would allow NAC and other antioxidant compounds and salts thereof to cross the BBB more readily. With significantly increased systemic concentration vs oral, a significant uptake of NAC or other antioxidant compound or salt is expected.

In some embodiments, the antioxidant compound is a small molecule. In some embodiments, the antioxidant compound is an enzyme. In some embodiments, the antioxidant compound is lipid soluble. In some embodiments, the antioxidant compound is water-soluble.

In some embodiments, the antioxidant compound is N-acetylcysteine. In some embodiments, the antioxidant compound is glutathione or a derivative thereof. In some embodiments, the antioxidant compound is coenzyme Q10. In some embodiments, the antioxidant compound is superoxide dismutase (SOD).

In some embodiments, the antioxidant compound is a pyrrolopyrimidine compound. In some embodiments, the antioxidant compound is a ubiquinone compound. In some embodiments, the antioxidant compound is a lazaroid compound.

In some embodiments, the antioxidant compound is selegiline. In some embodiments, the antioxidant compound is idebenone. In some embodiments, the antioxidant compound is probucol. In some embodiments, the antioxidant compound is tirilazad. In some embodiments, the antioxidant compound is memantine. In some embodiments, the antioxidant compound is ebselen. In some embodiments, the antioxidant compound is lipoic acid. In some embodiments, the antioxidant compound is vitamin E. In some embodiments, the antioxidant compound is vitamin C. In some embodiments, at least one antioxidant compound is a mixture of two or more of the aforementioned antioxidant compounds.

In some embodiments, the method further comprises administering a delivery agent to the subject. The delivery agent can be administered to the subject before, during or after the administration of the antioxidant compound. In some embodiments, a delivery agent is administered simultaneously with the antioxidant compound, such as when the antioxidant compound and the delivery agent are mixed in the same pharmaceutical formulation. In some embodiments, a delivery agent is administered before the administration of the antioxidant compound, for example, no more than about 15 seconds before, alternatively no more than about 30, 60, 90 or 120 seconds before, alternatively between 1 second and 10 minutes before the administration of the antioxidant compound.

In some embodiments, the method further comprises administering an anti-inflammatory agent to the subject. In some embodiments, the anti-inflammatory agent is a steroid. In some embodiments, the anti-inflammatory agent is a neurosteroid. In some embodiments, the anti-inflammatory agent is a lipophilic neurosteroid, a synthetic steroid, or a combination thereof. In some embodiments, the anti-inflammatory agent is progesterone.

In some embodiments, the anti-inflammatory agent is a non-steroidal compound. In some embodiments, the anti-inflammatory agent is trofinetide. In some embodiments, the anti-inflammatory agent comprises ghrelin or a variant thereof. In some embodiments, the anti-inflammatory agent is enoprofen, ibuprofen, indomethacin, naproxen, tolmetin, or a combination thereof.

In some embodiment, the anti-inflammatory agent is administered simultaneously with the at least one antioxidant compound. In some embodiments, the anti-inflammatory agent is administered prior to administering the at least one antioxidant compound to the subject. In some embodiments, the anti-inflammatory agent is sublingually or buccally administered to the subject.

In some embodiments, the method further comprises administering acetaminophen or aspirin. In some embodiment, acetaminophen or aspirin is administered simultaneously with the at least one antioxidant compound. In some embodiments, acetaminophen or aspirin is administered prior to administering the at least one antioxidant compound to the subject.

In some embodiments, the method further comprises administering to a subject an inhibitor of a puringergic receptor. In some embodiments, the purinergic receptor is P2X4, P2X7, P2Y6, or P2Y12. In some embodiments, the inhibitor of a purinergic receptor is a thienopyridine compound. In some embodiments, the inhibitor of a purinergic receptor is clopidogrel, prasugrel, ticlopidine, ticagrelor, cangreloror, or a combination thereof. In some embodiments, the inhibitor of a purinergic receptor is administered simultaneously with the at least one antioxidant compound. In some embodiments, the inhibitor of a purinergic receptor is administered prior to administering the at least one antioxidant compound to the subject. In some embodiments, the inhibitor of a purinergic receptor is sublingually or buccally administered to the subject.

In another embodiment, the present disclosure provides a method of treating a traumatic brain injury. The method comprises administering to a subject an effective amount of a pharmaceutical composition comprising at least one antioxidant compound, by sublingual or buccal administration.

In some embodiments, the antioxidant compound is a pyrrolopyrimidine compound, ubiquinone compound, a lazaroid compound, or a combination thereof. In some embodiments, the pharmaceutical compound is N-acetylcysteine, glutathione, co-enzyme Q-10, superoxide dismutase, or a combination thereof. In some embodiments, the antioxidant compound is present in a pharmaceutically acceptable salt in the sublingual or buccal dosage form.

In some embodiments, the pharmaceutical compound is an anti-inflammatory agent as described above. For example, in some embodiments, the anti-inflammatory agent is a steroid or a non-steroidal compound. In some embodiments, the anti-inflammatory agent is a neurosteroid. In some embodiments, the anti-inflammatory agent is progesterone, trofinetide, ghrelin or a variant thereof, or a combination thereof. In some embodiments, the anti-inflammatory agent is enoprofen, ibuprofen, indomethacin, naproxen, tolmetin, or a combination thereof. The anti-inflammatory agent may be administered separately or simultaneously with the at least one antioxidant compound. In some embodiments, the pharmaceutical compound is acetaminophen or aspirin.

When the subject is treated sublingually or buccally, the compounds or formulations of the present disclosure may be administered using any suitable delivery method. In some embodiments, a solution is applied directly to the oral mucosa or to a portion of the oral cavity.

In some embodiments, the antioxidant compound is as described above. In some embodiments, the antioxidant compound is a small molecule. In some embodiments, the antioxidant compound is an enzyme. In some embodiments, the antioxidant compound is a pyrrolopyrimidine compound, ubiquinone compound, a lazaroid compound, or a combination thereof. In some embodiments, the pharmaceutical compound is N-acetylcysteine, glutathione, co-enzyme Q-10, superoxide dismutase, or a combination thereof. In the present disclosure, references to the "antioxidant compound" should be understood to also refer to pharmaceutically acceptable salts, hydrates, solvates, and prodrugs of antioxidant compounds.

In some embodiments, the pharmaceutical formulation further comprises an anti-inflammatory agent as described above. For example, in some embodiments, the anti-inflammatory agent is a steroid or a non-steroidal compound. In some embodiments, the anti-inflammatory agent is progesterone, trofinetide, ghrelin or a variant thereof, or a combination thereof. In some embodiments, the anti-inflammatory agent is enoprofen, ibuprofen, indomethacin, naproxen, tolmetin, or a combination thereof.

In some embodiments, the sublingual or buccal dosage form further comprises an inhibitor of a puringergic receptor as described above. In some embodiments, the purinergic receptor is selected from the group consisting of P2X4, P2X7, P2Y6, and P2Y12. In some embodiments, the inhibitor of a purinergic receptor is clopidogrel, prasugrel, ticlopidine, ticagrelor, cangreloror, or a combination thereof.

Other delivery agents may be present in the pharmaceutical formulation. In some embodiments, delivery agents such as chitosan nanoparticles for mucoadhesion (e.g., pharmaceutical agent-loaded), micelles (e.g., lipophilic), or liposomal carriers such as archaeosomes, niosomes, novasomes, cyptosomes, emulsomes, and vesosomes are used to enhance delivery of the antioxidant compound to the brain. In some embodiments, the delivery agent can be an alkylsaccharide transmucosal delivery enhancement agent (such as Intravail®) which could increase the bioavailability of NAC, an absorption-enhancing water-based gel for transmucosal and transdermal drug delivery (such as Hydrogel™) or a pectin-based gelling agent (such as PecSys™) that can reduce drip and run-off.

In some embodiments, the sublingual or buccal dosage form comprises one or more excipients that aid permeation or are suitable for use in sublingual or buccal delivery. Some examples of excipients include pharmaceutically acceptable carriers are sugars, such as lactose, glucose and sucrose; starches such as corn starch and potato starch; cellulose and derivatives such as sodium carboxymethyl cellulose, ethyl cellulose and cellulose acetate; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as phosphates, carbonates, ascorbates, tartrates, borates, citrates, acetates, and maleates, for example magnesium hydroxide, aluminum hydroxide, monosodium phosphate, trisodium phosphate, ascorbic acid, sodium ascorbate, sodium hydroxide, sodium carbonate, sodium bicarbonate, sodium acid pyrophosphate, citric acid, sodium citrate, and combinations thereof; alginic acid; pyrogen free water; isotonic saline; solvents such as ethyl alcohol; and buffers such as phosphate buffer solutions, as well as other nontoxic compatible substances used in oral dosage forms. Wetting agents, emulsifiers and lubricants such as sodium lauryl sulfate and magnesium stearate, as well as coloring agents, release agents, coating agents, sweetening, flavoring and perfuming agents, preservatives and antioxidants can also be included in the present formulations.

In some embodiments, the sublingual or buccal dosage form comprises a fragrance or masking agent which alleviates the odor of the antioxidant compound. It is believed that the odor of a NAC formulation plays a critical role in the taste perception of the dosage form. When molecules are received into saliva or nasal mucus from fragrances or foods, they stimulate the sensory cells in the nose, mouth, or throat. When olfactory nerve cells are stimulated, an odor is perceived. Olfactory (smell) nerve cells are located high inside the nose, and connect directly to the brain. Gustatory (taste) nerve cells are located in the taste buds of the mouth and throat, and they sense the basic tastes of sweet, sour, bitter, salty and umami. Another chemosensory process, called common chemical sense, also contributes to smell and taste. These cells alert the brain to sensations such as heat (such as from peppers) or cool (such as from mints). Flavor is a combination of these senses working together and is highly dependent on olfaction. By reducing, masking or otherwise alleviating odor of the dosage form, it is expected that a subject will retain the sublingual or buccal dosage form in the oral cavity for a longer period of time, thereby providing a longer period for the oral mucosa to absorb the antioxidant compound. In comparison, if the dosage form is swallowed or spit out, rather than absorbed, some of the benefits of sublingual or buccal administration will be lost.

For sublingual and buccal administration, taste characteristics of NAC and other antioxidant compounds present difficult challenges, as they will activate taste receptors present within the oral cavity and throat, potentially eliciting unpleasant taste sensations such as bitterness or sourness. Taste is a distinct organoleptic attribute that will affect the overall sensory experience for patients in addition to odor.

In some embodiments, the sublingual or buccal dosage form comprises a masking agent, fragrance, chemical additive, or other component that alleviates (such as by improving, reducing or masking the odor and/or taste from NAC or other antioxidant compound. Examples of masking agents and fragrances include menthol, D-sorbitol, sodium acetate, adenosine 5'monophophaste, lecithin or lecithin-like substances, sweeteners such as sucrose or sucralose, effervescent agents such as sodium bicarbonate or citric acid, or an ion-exchange resin. In some embodiments, the sublingual or buccal dosage form comprises menthol as its masking agent or fragrance. A potential limitation with menthol is its strong smell, which may potentially be subjectively aversive to some patients. Accordingly, the content of menthol is selected carefully to provide effective masking of odor from the antioxidant compound to maintain smell intensity at a desirable level.

Menthol induces a cooling sensation by activating Transient Receptor Potential Melastatin 8 (TRPM8) channels. Other TRPM8 agonists include borneol, linalool, geraniol, hydroxy-citronellal, icilin, WS-12, Frescolat MGA, Frescolat ML, PMD 38, Coolact P, M8-Ag and Cooling Agent 10.

In some embodiments, the masking agent is a bitter-blocker, which is an agent that blocks or reduces bitter taste by interacting with the molecular pathway of bitterness at a molecular or cellular level. Examples of bitter-blockers include adenosine 5'monophophaste, Beta-cyclodextrin (HPBCD), sodium acetate, sodium gluconate, cyclamate, inhibitors or gastducin, inhibitors of taste 2 receptor family (TAS2Rs or T2Rs) proteins, and inhibitors of P2X2/P2X3 receptors. In some embodiments, NAC is included as a complex with a cyclodextrin or ion exchange resin. For example, NAC can be incorporated into the cavity of a cyclodextrin, for instance, (2-Hydroxypropyl)-β-cyclodextrin (HP-β-CyD) also known as (2-hydroxypropyl) beta-cyclodextrin (HPBCD). Other examples of cyclodextrins include methyl-β-cyclodextrin, sulfobutyl-β-cyclodextrin, and hydroxypropyl-γ-cyclodextrin. In some embodiments, the bitter-blocker is an agent that does not increase astringency taste. Other information regarding bitter-blockers may be found in Andrews et al., "Bitter-blockers as a taste masking strategy: A systematic review towards their utility in pharmaceuticals." Eur J Pharm Biopharm. 2021. 158:35-51.

It is contemplated that the content of any of the masking agent(s), fragrances(s), chemical additive(s), or other component(s) disclosed herein (including but not limited to menthol, vanillin, a cyclodextrin such as HPBCD, or an additional antioxidant), either individually or in total, in the sublingual or buccal dosage form can be at least 0.001%, or at least 0.002%, or at least 0.003%, or at least 0.004%, or at least 0.005%, or at least 0.006%, or at least 0.007%, or at least 0.008%, or at least 0.009%, at least 0.01%, or at least 0.011%, or at least 0.012%, or at least 0.013%, or at least 0.014%, or at least 0.015%, or at least 0.016%, or at least 0.017%, or at least 0.018%, or at least 0.019%, or at least 0.02%, or at least 0.021%, or at least 0.022%, or at least 0.023%, or at least 0.024%, or at least 0.025%, or at least 0.026%, or at least 0.027%, or at least 0.028%, or at least 0.029%, or at least 0.03%, or at least 0.031%, or at least 0.032%, or at least 0.033%, or at least 0.034%, or at least 0.035%, or at least 0.036%, or at least 0.037%, or at least 0.038%, or at least 0.039%, or at least 0.04%, or at least 0.041%, or at least 0.042%, or at least 0.043%, or at least 0.044%, or at least 0.045%, or at least 0.046%, or at least 0.047%, or at least 0.048%, or at least 0.049%, or at least 0.05%, or at least 0.051%, or at least 0.052%, or at least 0.053%, or at least 0.054%, or at least 0.055%, or at least 0.056%, or at least 0.057%, or at least 0.058%, or at least 0.059%, or at least 0.06%, or at least 0.061%, or at least 0.062%, or at least 0.063%, or at least 0.064%, or at least 0.065%, or at least 0.066%, or at least 0.067%, or at least 0.068%, or at least 0.069%, or at least 0.07%, or at least 0.071%, or at least 0.072%, or at least 0.073%, or at least 0.074%, or at least 0.075%, or at least 0.076%, or at least 0.077%, or at least 0.078%, or at least 0.079%, or at least 0.08%, or at least 0.081%, or at least 0.082%, or at least 0.083%, or at least 0.084%, or at least 0.085%, or at least 0.086%, or at least 0.087%, or at least 0.088%, or at least 0.089%, or at least 0.09%, or at least 0.091%, or at least 0.092%, or at least 0.093%, or at least 0.094%, or at least 0.095%, or at least 0.096%, or at least 0.097%, or at least 0.098%, or at least 0.099%, at least 0.1%, or at least 0.11%, or at least 0.111%, or at least 0.112%, or at least 0.113%, or at least 0.114%, or at least 0.115%, or at least 0.116%, or at least 0.117%, or at least 0.118%, or at least 0.119%, or at least 0.12%, or at least 0.121%, or at least 0.122%, or at least 0.123%, or at least 0.124%, or at least 0.125%, or at least 0.126%, or at least 0.127%, or at least 0.128%, or at least 0.129%, or at least 0.13%, or at least 0.1325%, or at least 0.135%, or at least 0.1375%, or at least 0.14%, or at least 0.1425%, or at least 0.145%, or at least 0.1475%, or at least 0.15%, or at least 0.1525%, or at least 0.155%, or at least 0.1575%, or at least 0.16%, or at least 0.1625%, or at least 0.165%, or at least 0.1675%, or at least 0.17%, or at least 0.1725%, or at least 0.175%, or at least 0.1775%, or at least 0.18%, or at least 0.1825%, or at least 0.185%, or at least 0.1875%, or at least 0.19%, or at least 0.1925%, or at least 0.195%, or at least 0.1975%, or at least 0.2%, or at least 0.21%, or at least 0.22%, or at least 0.23%, or at least 0.24%, or at least 0.25%, or at least 0.26%, or at least 0.27%, or at least 0.28%, or at least 0.29%, or at least 0.3%, or at least 0.31%, or at least 0.32%, or at least 0.33%, or at least 0.34%, or at least 0.35%, or at least 0.36%, or at least 0.37%, or at least 0.38%, or at least 0.39%, or at least 0.4%, by weight. Alternatively or additionally, the content of any of the masking agent(s), fragrances(s), chemical additive(s), or other component(s) disclosed herein (including but not limited to menthol, vanillin, a cyclodextrin such as HPBCD, or an additional antioxidant), either individually or in total, in the sublingual or buccal dosage form can be at most 10%, or at most 9%, or at most 8%, or at most 7%, or at most 6%, or at most 5.5%, or at most 5%, or at most 4.5%, or at most 4%, or at most 3.5%, or at most 3%, or at most 2.5%, or at most 2%, or at most 1.5%, or at most 1.4%, or at most 1.3%, or at most 1.2%, or at most 1.1%, or at most 1%, or at most 0.95%, or at most 0.9%, or at most 0.85%, or at most 0.8%, or at most 0.75%, or at most 0.7%, or at most 0.65%, or at most 0.6%, or at most 0.575%, or at most 0.55%, or at most 0.525%, or at most 0.5%, or at most 0.475%, or at most 0.45%, or at most 0.425%, or at most 0.4%, or at most 0.375%, or at most 0.35%, or at most 0.325%, or at most 0.3%, or at most 0.29%, or at most 0.28%, or at most 0.27%, or at most 0.26%, or at most 0.25%, or at most 0.24%, or at most 0.23%, or at most 0.22%, or at most 0.21%, or at most 0.2%, or at most 0.19%, or at most 0.18%, or at most 0.17%, or at most 0.16%, or at most 0.15%, or at most 0.14%, or at most 0.13%, or at most 0.1275%, or at most 0.125%, or at most 0.1225%, or at most 0.12%, or at most 0.119%, or at most 0.118%, or at most 0.117%, or at most 0.116%, or at most 0.115%, or at most 0.114%, or at most 0.113%, or at most 0.112%, or at most 0.111%, or at most 0.11%, or at most 0.109%, or at most 0.108%, or at most 0.107%, or at most 0.106%, or at most 0.105%, or at most 0.104%, or at most 0.103%, or at most 0.102%, or at most 0.101%, or at most 0.1005%, or at most 0.1%, or at most 0.0995%, or at most 0.099%, or at most 0.098%, or at most 0.097%, or at most 0.096%, or at most 0.095%, or at most 0.094%, or at most 0.093%, or at most 0.092%, or at most 0.091%, or at most 0.09%, or at most 0.089%, or at most 0.088%, or at most 0.087%, or at most 0.086%, or at most 0.085%, or at most 0.084%, or at most 0.083%, or at most 0.082%, or at most 0.081%, or at most 0.08%; it is contemplated that any of the foregoing minima and maxima can be combined to form a range so long as the minimum is less than the maximum.

In some embodiments, the sublingual or buccal dosage form is manufactured in a manner that alleviates odor or taste properties of the dosage form. For example, the sublingual or buccal dosage form can be manufactured by a process that includes coating with a polymer, granulation, spray congealing with lipids, freeze drying, or formation of inclusion complexes with cyclodextrins. In some embodiments, the sublingual or buccal dosage form is manufactured by deoxygenating the antioxidant compound before its inclusion in the dosage form, such as by passing nitrogen gas through a solution comprising the antioxidant compound. In some embodiments, the sublingual or buccal dosage form comprises deoxygenated NAC or other deoxygenated antioxidant compound.

In some embodiments, a sublingual or buccal dosage form comprises both rapid and slow soluble components when introduced into the oral cavity as a function of the two distinct formulations within the single dosage form or dosage applicator. Sublingual or buccal dosage forms (comprising fast and slow absorption components) may be characterized by their dissolution times in vitro. Sublingual or buccal dosage forms (comprising fast and slow absorption components) typically exhibit a dissolution time of about ten seconds to about 100 minutes. In some embodiments, the dosage forms exhibit a dissolution time from about ten seconds to about 50 minutes, or from about 10 seconds to about 30 minutes, or from about 10 seconds to about 20 minutes.

In some embodiments, a sublingual or buccal dosage form has a longer shelf-life and stability compared to other dosage forms or formulations. For instance, sublingual or buccal dosage form can have a shelf-life of at least three months, or at least six months, or longer. In some embodiments, a sublingual or buccal dosage form is an alternative to intra-nasal delivery when the antioxidant compound, such as NAC, has a strong, sulfur-like smell, which some people may not able or willing to tolerate. In some embodiments, the present methods comprise administering the sublingual or buccal dosage form to a subject unable or unwilling to tolerate ingestion or intranasal administration of the at least one antioxidant compound or salt thereof, for example, a subject whose previous use of NAC for a long period has irritated the nasal epithelium.

In some embodiments, the sublingual or buccal dosage form is a lozenge, hard candy, lollypop, soft candy, chewing gum, patch, or film. The lozenge can be a single layer lozenge, a multilayer lozenge, or a core-shell lozenge.

In some embodiments, the buccal dosage form is a film, e.g. a buccal film. The mechanical, bioadhesive, and swelling properties of films are controlled to be suitable for buccal administration. Films for buccal administration are preferably flexible, elastic, soft yet sufficiently strong to withstand breakage due to stress from handling such as unwrapping and mouth action and also exhibit good bioadhesiveness so as to be retained in the mouth for a desired duration. Swelling of films is preferably avoided or limited, to prevent discomfort.

In some embodiments, the sublingual or buccal dosage form (e.g., a dissolvable strip) comprises up to 120 mg (e.g., from 0.1 to 60 mg) of an antioxidant compound such as NAC. In some embodiments, up to 180 mg (e.g., from 30 to 90 mg) of a water-soluble polymer, up to 80 mg (e.g., from 20 to 40 mg) of a plasticizer, up to 24 mg (e.g., from 6 mg to 12 mg) of a sweetening agent, and up to 24 mg (e.g., from 4 mg to 12 mg) of a saliva stimulating agent.

In some embodiments, the sublingual or buccal dosage form comprises a water-soluble polymer, such as one or more of HPMC E3, E5 and E15 and K-3, Methyl cellulose A-3, A-6 and A-15, Pullulan, carboxymethylcellulose cekol 30, polyvinylpyrrolidone PVP K-90, pectin, gelatin, sodium, alginate, hydroxypropyl cellulose, polyvinyl alcohol, or maltodextrins.

In some embodiments, the sublingual or buccal dosage form comprises a disintegrant. Exemplary disintegrants include, but are not limited to, sodium starch glycolate, crospovidone, croscarmellose sodium, low-substituted hydroxypropyl cellulose, starch, pregelatinized starch, microcrystalline cellulose, and mixtures thereof. In some embodiments, the content of the disintegrant in the sublingual or buccal dosage form may be from about 0.5% to about 25%, from about 1% to about 20%, from about 2% to about 15%, or from about 3% to about 9% weight/weight per dosage unit. The proportion of the disintegrant in the sublingual or buccal dosage form can be 0.1 to 75%, or 1 to 60%, or 1 to 40%, by weight.

In some embodiments, the sublingual or buccal dosage form comprises a plasticizer, such as one or more of glycerol, dibutyl phthalate, or polyethylene glycol.

In some embodiments, the sublingual or buccal dosage form comprises a sweetening agent, such as mannitol, maltitol, sorbitol, sucrose, sucralose, dextrose, saccharin, cyclamate, aspartame, or a combination thereof. Sweetening agents can be used for masking unpleasant taste that the antioxidant compound may have. Examples of sweetening agents include, but are not limited to, saccharide families such as mono-, di-, tri-, poly-, and oligosaccharides; sucrose, glucose (corn syrup), dextrose, fructose, maltodextrin and sugars such as polydextrose; saccharin and its salts such as sodium and calcium salts; cyclamic acid and its salts; dipeptide sweetening agents; chlorinated sugar derivatives such as sucralose and dihydrochalcone; sorbitol, sorbitol syrup, mannitol, and xylitol. In some embodiments, the sublingual or buccal dosage form comprises from about 0.01% to about 20%, alternatively from about 0.1% to about 10%, alternatively from about 0.5% to about 5% by weight sweetening agent.

In some embodiments, the sublingual or buccal dosage form comprises a saliva stimulating agent such as one or more of citric acid, malic acid, lactic acid, or ascorbic acid.

In some embodiments, the sublingual or buccal dosage form further comprises one or more surfactants, such as sodium lauryl sulfate, benzalkonium chloride, or Tween.

In some embodiments, the sublingual or buccal dosage form further comprises one or more fillers, such as one or more of mannitol, lactose, xylitol, other saccharides, and mixtures thereof. In some embodiments, the saccharide filler is anhydrous.

In some embodiments, the sublingual or buccal dosage form, further comprises one or more binders (e.g., Kollidon povidones, copovidones, and crospovidone, polyvinyl pyrolidone, hydroxymethyl polyvinyl pyrolidone, and gelatin). A binder can be used to prevent unnecessary reduction in the rate of dissolution for each of the "fast" and "slow" dissolution aspect of the dosage form. Preferred binders are soluble in water. Preferred binders aremay also be used.

In some embodiments, the sublingual or buccal dosage form further comprises one or more coloring agents, such as FD&C colors like FD&C Blue No. 1 (Brilliant Blue FCF), FD&C Blue No. 2 (Indigotine), FD&C Green No. 3 (Fast Green FCF), FD&C Red No. 3 (Erythrosine), FD&C Yellow No. 5 (Tartrazine), and FD&C Yellow No. 6 (Sunset Yellow).

In some embodiments, the sublingual or buccal dosage form further comprises one or more flavoring agents, such as US FDA approved flavors. Examples of flavoring agents include lemonoil, orange oil, peppermint oil, methyl salicylate, allyl benzoate, allyl caproate, and yara yara. Other examples of flavoring agents are vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, and licorice.

A small proportion of lubricant may be used, for example up to 1%, preferably about 0.8%. Use of an extra-granular lubricant alone is preferred in order to minimize the hydrophobic properties of the dosage form.

The sublingual or buccal dosage form may include excipients typically present in such compositions. These may include flavoring agents. Flavoring agents when used are typically present up to about 0.5 to 5% by weight of the whole tablet. Sweetening agents and other excipients such as coloring agents, preservatives and fillers may be included.

In some embodiments, the sublingual or buccal dosage form is a disintegrating dosage form. Disintegrating dosage forms generally have superior bioavailability, faster pregastric absorption and higher rates of patient compliance compared to oral dosage forms. Disintegrating dosage forms can be an alternative with a much higher patient compliance rate.

In some embodiments, an antioxidant compound or salt thereof in particles of a particular particle size is complexed with or administered together with a second agent, e.g., an agent that facilitates penetration of the antioxidant compound or salt thereof into a tissue, into cells, or into the blood stream. In one embodiment, an antioxidant compound or salt thereof is provided together with a permeation enhancer.

Exemplary agents enhancing uptake of an antioxidant compound into cells include fatty acids, derivatives of fatty acids, lipids or complexes of lipids or comprising lipids, e.g., liposomes. Liposomes are hollow spherical vesicles composed of lipids arranged in a similar fashion as those lipids which make up the cell membrane. They may have an internal aqueous space for entrapping water soluble compounds and range in size from 0.05 to several microns in diameter. For example, a liposome delivery vehicle originally designed as a research tool, Lipofectin, has been shown to deliver intact molecules to cells. Liposomes offer several advantages: they are non-toxic and biodegradable in composition; they display long circulation half-lives; and recognition molecules can be readily attached to their surface for targeting to tissues. Lipid aggregates can be formed with macromolecules using, e.g., cationic lipids alone or including other lipids and amphiphiles such as phosphatidylethanolamine. Liposomes comprising cationic lipids are favored for delivery of negatively charged molecules.

Agents may also be provided together with a sustained release mechanism, which may include, e.g., polymer microspheres, and other mechanisms known to those skilled in the art to vary the rate of release of an agent. Accordingly, an active agent may be provided together with at least one permeation or permeability enhancer, and/or optionally, may comprise at least one sustained release mechanism and/or at least one bioadhesive. Examples of permeation enhancers include, but not limited to, fatty acids, Cavitron, thiomers, and polyoxyethylene.

In some embodiments, the pharmaceutical formulation comprises an additional antioxidant to prevent NAC oxidation, such as adipic acid, ascorbic acid, ascorbyl palmitate, butylated hydroxyanisole, butylated hydroxytoluene (BHT), citric acid, dithiothreitol, ethylenediaminetetraacetic acid (EDTA), fumaric acid, glutamic acid, malic acid, propyl gallate, sodium ascorbate, sodium formaldehyde sulfoxylate, sodium metabisulfite, sodium sulfite, sodium thiosulfate, tartaric acid, thioglycerol, throurea, tocopherols, p-toluene sulfonic acid, or combinations thereof. In some embodiments, the dosage form comprises two, three, or more additional antioxidants.

In another embodiment, the present disclosure provides a kit for treating a subject having a central nervous system (CNS) disorder. The kit comprises (a) a sublingual or buccal dosage form comprising at least one antioxidant compound or a pharmaceutically acceptable salt thereof, and (b) an intranasal dosage form comprising the antioxidant compound or salt thereof. In some embodiments, the kit further comprises an intranasal delivery device.

In some embodiments, the present kits comprise one or more containers with agents other than an antioxidant compound. For instance, a kit can comprise separate containers of an agent for enhancing delivery of and/or alleviating odor from an antioxidant compound. In some embodiments, the present kits comprise one or more containers that contain a fragrance or a masking agent, such as a cyclodextrin compound (e.g., (2-hydroxypropyl) beta-cyclodextrin (HPBCD)).

In some embodiments, the antioxidant compound is as described above. For example, in some embodiments, the antioxidant compound is selected from the group consisting of N-acetylcysteine, glutathione, co-enzyme Q-10, superoxide dismutase (SOD), and a combination thereof.

In some embodiments, the kit comprises instructions for using the components of the kit. In some embodiments, the kit comprises instructions for mixing the separate components, suitable conditions for the components and/or mixture, and/or suitable vessels for mixing the composition. Where a kit comprises a plurality of containers, the kit can also include instructions that direct how to use the respective containers, such as the order and timing of use.

The instructions may contain how often to apply the antioxidant compound, and/or the time for administration after an initial injury, and/or the timing of application between sublingual and/or buccal administration, and administration by a different route. In some embodiments, the instructions include the length of treatment and how often each day it should be administered. In some embodiments, the instructions may also include dosing amounts based on a subject's age, weight and/or how severe a subject's head injury is.

In some embodiments, the kit further comprises one or more additional compounds. For example, the kit may further comprise an anti-inflammatory agent, purinergic receptor inhibitor, or another drug delivery agent such as micelles (e.g., lipophilic), or liposomal carriers as described above. The kit may further comprise a delivery enhancing agent, a masking agent, an odor suppressing agent, a fragrance, an analgesic, or other agents. In some embodiments, the additional compounds are provided in the same or separate containers.

The sublingual or buccal dosage forms and methods of the present disclosure may be used to treat any central nervous system disorder. In some embodiments, the sublingual or buccal dosage forms and methods of the present disclosure are used to treat a central nervous system disorder involving oxidative stress. In some embodiments, the sublingual or buccal dosage forms and methods of the present disclosure are used to treat a central nervous system disorder resulting from injury, autoimmune disease, or a degenerative disorder. In some embodiments, the sublingual or buccal dosage forms and methods of the present disclosure are used to treat a traumatic brain injury. In some embodiments, the central nervous system disorder is selected from traumatic brain injury (TBI) (including mild TBI, moderate TBI, or severe TBI), chronic traumatic encephalopathy (CTE), post-concussive syndrome, Parkinson's disease, Huntington's disease, stroke, depression, bi-polar disorder, Alzheimer's disease, MS and amyotrophic lateral sclerosis (ALS).

In some embodiments, the methods and compositions of the present disclosure are used to treat a neurodegenerative disorder. In some embodiments, the sublingual or buccal dosage forms and methods of the present disclosure are used to treat Alzheimer's disease. In some embodiments, the sublingual or buccal dosage forms and methods of the present disclosure are used to treat Parkinson's disease. In some embodiments, the sublingual or buccal dosage forms and methods of the present disclosure are used to treat Huntington's disease. In some embodiments, the sublingual or buccal dosage forms and methods of the present disclosure are used to treat amyotrophic lateral sclerosis (ALS). In some embodiments, the sublingual or buccal dosage forms and methods of the present disclosure are used to treat dementia. In some embodiments, the sublingual or buccal dosage forms and methods of the present disclosure are used to treat stroke.

In some embodiments, the sublingual or buccal dosage forms and methods of the present disclosure are used to treat multiple sclerosis (MS). In some embodiments, the sublingual or buccal dosage forms and methods of the present disclosure are used to treat epilepsy. In some embodiments, the sublingual or buccal dosage forms and methods of the present disclosure are used to treat a central nervous system disorder resulting from a stroke, tumor, or an infection. In some embodiments, the sublingual or buccal dosage forms and methods of the present disclosure are used to treat autism, obsessive compulsive disorder (OCD), schizophrenia, alcohol addition, drug addiction, gambling addiction, sex addiction, depression, anxiety, epilepsy, damage caused by seizures due to epilepsy, damage caused by nerve agents, damage caused by seizures due to nerve agent exposure, alphaviruses, damage to brain caused by alphaviruses, coronaviruses, damage to brain caused by coronaviruses, including brain fog and other side effects from coronaviruses.

In some embodiments, the present methods comprise sublingual or buccal administration to a subject in need of treatment for a chronic disorder. Intranasal delivery may not be suitable for a chronic illness due to possible irritation to the nasal epithelium. In some embodiments, a method of treating a chronic disorder comprises intranasal administration of NAC or other antioxidant compound for a first treatment period (e.g., 1 week), followed by sublingual or buccal administration of NAC or another antioxidant compound for a second treatment period (e.g., 3 weeks). The method can further comprise a third treatment period after the second, wherein NAC or an antioxidant compound is intranasally administered, followed by a fourth treatment period (e.g., 3 weeks) of sublingual or buccal administration. These treatment periods can be repeated for one, two, three or more additional cycles.

In some embodiments, intranasal administration of NAC may be supplemented by sublingual or buccal administration of NAC or other antioxidant compound, such as for acute injuries such as concussions, which may allow more drug to offset the secondary injury from a concussion. In some embodiments, a sublingual or buccal dosage form of NAC may be administered to a subject as an initial dose after an injury, followed by intranasal administration of NAC. This can be advantageous for subjects in need of treatment for an acute injury.

In some embodiments, the sublingual or buccal dosage forms and methods of the present disclosure are used to treat hearing loss, such as conductive hearing loss, sensorineural hearing loss, or mixed hearing loss. For example, the sublingual or buccal dosage forms and methods can be used to treat noise induced hearing loss. The hearing loss can be caused by or accompanying traumatic brain injury, or can be independent of traumatic brain injury. In some embodiments, the sublingual or buccal dosage forms and methods of the present disclosure are used to treat blast-induced hearing loss from an explosion such as an IED. In some embodiments, the sublingual or buccal dosage forms and methods of the present disclosure are used to treat age-related hearing loss (presbycusis).

The pharmaceutical compounds of the present disclosure (e.g., antioxidant compound) may be administered to a subject using any suitable dosage regimen. In some embodiments, the pharmaceutical compound is administered to a subject for at least 1 day. In some embodiments, the pharmaceutical compound is administered to a subject for at least 2 days. In some embodiments, the pharmaceutical compound is administered to a subject for at least 3 days. In some embodiments, the pharmaceutical compound is administered to a subject for at least 4 days. In some embodiments, the pharmaceutical compound is administered to a subject for at least 5 days. In some embodiments, the pharmaceutical compound is administered to a subject for at least 6 days. In some embodiments, the pharmaceutical compound is administered to a subject for at least 7 days. In some embodiments, the pharmaceutical compound is administered to a subject for at least 8 days. In some embodiments, the pharmaceutical compound is administered to a subject for at least 9 days. In some embodiments, the pharmaceutical compound is administered to a subject for at least 10 days. In some embodiments, the pharmaceutical compound is administered to a subject for at least 14 days. In some embodiments, the pharmaceutical compound is administered to a subject for an indefinite period, such as when the subject has a chronic disorder. The pharmaceutical compound may be separately dosed or administered simultaneously with at least one anti-inflammatory agent, inhibitor of a purinergic receptor, or delivery agent as described above.

In some embodiments, the pharmaceutical compound (e.g., antioxidant compound) is administered once daily. In some embodiments, two doses of pharmaceutical compound (e.g., antioxidant compound) are administered daily. In some embodiments, the pharmaceutical compound (e.g., antioxidant compound) is administered once daily for 1 to 30 days or for a longer period, such as 1 to 60 or 1 to 90 days, or for a period of 7, 14, 28, 56, or 84 days. In some embodiments, the pharmaceutical compound is administered for a first treatment period (e.g., 1 week), followed by sublingual or buccal administration of the same or different pharmaceutical compound for a second treatment period (e.g., 3 weeks). The method can further comprise a third treatment period after the second, wherein a pharmaceutical compound is intranasally administered, followed by a fourth treatment period (e.g., 3 weeks) of sublingual or buccal administration. These treatment periods can be repeated for one, two, three or more additional cycles In some embodiments, the pharmaceutical compound (e.g., antioxidant compound) is administered once daily for 5 to 7 days. In some embodiments, two doses of pharmaceutical compound (e.g., antioxidant compound) are administered daily for 5 to 7 days. The dosing regimen may depend on the half-life of the pharmaceutical compound (e.g., antioxidant compound). The pharmaceutical compound (e.g., antioxidant compound) may be separately dosed or administered simultaneously with any anti-inflammatory agent, inhibitor of a purinergic receptor, or delivery agent, as described above.

In some embodiments, the present methods further comprise obtaining a MRS scan, bloodwork or saliva biomarker from a subject to determine the glutathione level in the brain or blood of the subject, and determining a dose amount, timing, cadence and route of delivery (between sublingual/buccal and intranasal for example), based on the determined glutathione level.

In some embodiments, at least one antioxidant compound is administered to a subject having a traumatic brain injury. Rapid and targeted delivery of the antioxidant compound following traumatic brain injury may arrest or reduce oxidative cascade reactions in the brain of the subject. In some embodiments, the antioxidant compound is administered to the subject immediately after traumatic brain injury. In some embodiments, the antioxidant compound is administered to the subject within 5 minutes, 10 minutes, 15 minutes, or 30 minutes of traumatic brain injury. In some embodiments, the antioxidant compound is administered to the subject within 1 hour of traumatic brain injury. In some embodiments, the antioxidant compound is administered to the subject within 2 hours of traumatic brain injury. In some embodiments, the antioxidant compound is administered to the subject within 4 hours of traumatic brain injury. In some embodiments, the antioxidant compound is administered to the subject within 6 hours of traumatic brain injury. In some embodiments, the antioxidant compound is administered to the subject within 12 hours of traumatic brain injury. In some embodiments, the antioxidant compound is administered to the subject within 16 hours of traumatic brain injury. In some embodiments, the antioxidant compound is administered to the subject within 24 hours of traumatic brain injury. In some embodiments, the antioxidant compound is administered to the subject within 2 days of traumatic brain injury. The antioxidant compound may be separately dosed or administered simultaneously with any anti-inflammatory agent, inhibitor of a purinergic receptor, or delivery agent as described above. Sublingually or buccally administering the antioxidant compound (e.g., by a first responder), alone or in combination with at least one pharmaceutical or delivery agent, may allow for immediate treatment of a subject suffering from a traumatic brain injury.

The pharmaceutical compounds (e.g., antioxidant compound) of the present disclosure can be administered in any suitable amount to treat a central nervous system disorder (e.g., traumatic brain injury). In some embodiments, the total daily dose of a pharmaceutical compound (e.g., an antioxidant compound) (administered in single or divided doses) is from about 0.001 to about 100 mg/kg (i.e., mg of the compound or salt per kg body weight). Thus, in some embodiments, the total daily dose of the antioxidant compound (administered in single or divided doses) is from about 0.001 to about 100 mg/kg, from 0.001 to about 50 mg/kg, from 0.001 to about 30 mg/kg, from 0.001 to about 20 mg/kg, or from about 0.01 to about 10 mg/kg (i.e., mg of the compound or salt per kg body weight). In some embodiments, dosage unit compositions contain such amounts or submultiples thereof to make up the daily dose. In some embodiments, multiple doses per day may be used to increase the total daily dose, if desired. The amount of pharmaceutical compound may need to be adjusted based on severity, age, severity of concussion, weight, and/or size of the subject suffering from the central nervous system disorder (e.g., traumatic brain injury).

The methods and sublingual or buccal dosage forms of the present disclosure may be applied to a subject such as a human, non-human primate, or a domesticated or semi-domesticated animal. The subject may be a cow, sheep, goat, pig, horse, dog, cat, rabbit, rat, mouse, or the like. In some embodiments, the subject is a mammal. In some embodiments, the subject is a primate. In some embodiments, the subject is a human.

In addition to the sublingual and buccal dosage forms discussed herein, the pharmaceutical compounds of the present disclosure may additionally be provided in other forms suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present disclosure may be a pharmaceutically acceptable salt. Representative pharmaceutically acceptable salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate, lactate, maleate, methanesulfonate, nicotinate, 2-naphthalenesulfonate, oxalate, pamoate, pectinate, persulfate, picrate, pivalate, propionate, succinate, tartrate, thiocyanate, phosphate, glutamate, bicarbonate, p-toluenesulfonate, and undecanoate.

The antioxidant compounds may be in prodrug form. Prodrugs are derivatives, which convert into the active agent when introduced into the subject in which they are used, by a chemical or biological process in vivo.

It is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

As disclosed herein, when a percentage of a component is provided, it indicates the percentage on a weight basis (w/w) unless the context indicates otherwise.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

All patents and publications referred to herein are expressly incorporated by reference in their entireties. The citation of any publication is for its disclosure prior to the filing date and should not be construed as an admission that the present claims are not entitled to antedate such publication. Further, the dates of publication provided can be different from the actual publication dates which can be independently confirmed.

As used in the specification and appended claims, the terms "a", "an," and "the" include both singular and plural referents, unless the context clearly dictates otherwise. Thus, for example, "a moiety" includes one moiety and plural moieties.

EXAMPLES

Example 1A

A sublingual or buccal dosage form comprises from 0.1 to 60 mg NAC, approximately 90 mg of a water-soluble polymer, approximately 40 mg of a plasticizer, from 6 mg to 12 mg of a sweetening agent, and from 4 mg to 12 mg of a saliva stimulating agent.

Example 1B

A sublingual or buccal dosage form comprises from 0.1 to 60 mg NAC, approximately 40 mg of a plasticizer, from 6 mg to 12 mg of a sweetening agent, from 4 mg to 12 mg of a saliva stimulating agent, and approximately 90 mg of one or more of HPMC E3, E5 and E15 and K-3, Methyl cellulose A-3, A-6 and A-15, Pullulan, carboxymethylcellulose cekol 30, polyvinylpyrrolidone PVP K-90, pectin, gelatin, sodium, alginate, hydroxypropyl cellulose, polyvinyl alcohol, or maltodextrins.

Example 1C

A sublingual or buccal dosage form comprises from 0.1 to 60 mg NAC, approximately 90 mg of a water-soluble polymer, from 6 mg to 12 mg of a sweetening agent, from 4 mg to 12 mg of a saliva stimulating agent, and approximately 40 mg of one or more of glycerol, dibutyl phthalate, or polyethylene glycol.

Example 1D

A sublingual or buccal dosage form comprises from 0.1 to 60 mg NAC, approximately 90 mg of a water-soluble polymer, approximately 40 mg of a plasticizer, from 4 mg to 12 mg of a saliva stimulating agent, and from 6 mg to 12 mg of one or more of saccharin, cyclamate, or aspartame.

Example 1E

A sublingual or buccal dosage form comprises from 0.1 to 60 mg NAC, approximately 90 mg of a water-soluble polymer, approximately 40 mg of a plasticizer, from 6 mg to 12 mg of a sweetening agent, and from 4 mg to 12 mg of one or more of citric acid, malic acid, lactic acid, or ascorbic acid, or a salt thereof.

Example 1F

A sublingual or buccal dosage form comprises from 0.1 to 60 mg NAC, approximately 90 mg of a water-soluble polymer, approximately 40 mg of a plasticizer, from 6 mg to 12 mg of a sweetening agent, and from 4 mg to 12 mg of a saliva stimulating agent, and sodium lauryl sulfate, benzalkonium chloride, or Tween.

Example 1G

A sublingual or buccal dosage form comprises from 0.1 to 60 mg NAC, approximately 90 mg of a water-soluble polymer, approximately 40 mg of a plasticizer, from 6 mg to 12 mg of a sweetening agent, from 4 mg to 12 mg of a saliva stimulating agent, and one or more fillers.

Example 2A

A sublingual or buccal dosage form comprises up to 120 mg NAC, approximately 180 mg of a water-soluble polymer, approximately 80 mg of a plasticizer, up to 24 mg of a sweetening agent, and up to 24 mg of a saliva stimulating agent.

Example 2B

A sublingual or buccal dosage form comprises up to 120 mg NAC, approximately 80 mg of a plasticizer, up to 24 mg of a sweetening agent, up to 24 mg of a saliva stimulating agent, and approximately 180 mg of one or more of HPMC E3, E5 and E15 and K-3, Methyl cellulose A-3, A-6 and A-15, Pullulan, carboxymethylcellulose cekol 30, polyvinylpyrrolidone PVP K-90, pectin, gelatin, sodium, alginate, hydroxypropyl cellulose, polyvinyl alcohol, or maltodextrins.

Example 2C

A sublingual or buccal dosage form comprises up to 120 mg NAC, approximately 180 mg of a water-soluble polymer, up to 24 mg of a sweetening agent, up to 24 mg of a saliva stimulating agent, and approximately 80 mg of one or more of glycerol, dibutyl phthalate, or polyethylene glycol.

Example 2D

A sublingual or buccal dosage form comprises up to 120 mg NAC, approximately 180 mg of a water-soluble polymer, approximately 80 mg of a plasticizer, up to 24 mg of a saliva stimulating agent, and up to 24 mg of one or more of saccharin, cyclamate, or aspartame.

Example 2E

A sublingual or buccal dosage form comprises up to 120 mg NAC, approximately 180 mg of a water-soluble polymer, approximately 80 mg of a plasticizer, up to 24 mg of a sweetening agent, and up to 24 mg of one or more of citric acid, malic acid, lactic acid, or ascorbic acid, or a salt thereof.

Example 2F

A sublingual or buccal dosage form comprises up to 120 mg NAC, approximately 180 mg of a water-soluble polymer, approximately 80 mg of a plasticizer, up to 24 mg of a sweetening agent, and up to 24 mg of a saliva stimulating agent, and sodium lauryl sulfate, benzalkonium chloride, or Tween.

Example 2G

A sublingual or buccal dosage form comprises up to 120 mg NAC, approximately 180 mg of a water-soluble polymer, approximately 80 mg of a plasticizer, up to 24 mg of a sweetening agent, up to 24 mg of a saliva stimulating agent, and one or more fillers.

Example 3A

A dissolvable strip comprises from 0.1 to 60 mg NAC, a binder, a disintegrant, and a sweetener or flavoring agent.

Example 3B

A dissolvable strip comprises up to 120 mg NAC, a binder, and a disintegrant, and a sweetener or flavoring agent.

Example 4A

In this example, a study evaluates a sublingual or buccal dosage form comprising N-acetyl cysteine. GSH levels in the blood and/or GSH levels in the brain of non-human subjects resulting from the sublingual or buccal dosage form will be compared via magnetic resonance spectroscopy to GSH levels resulting from an oral dosage form.

Example 4B

Another study compares GSH levels in the blood and/or GSH levels in the brain of non-human subjects resulting from administration of a sublingual or buccal dosage form to GSH levels from intranasal administration.

Example 4C

Another study compares GSH levels in the blood of human subjects resulting from the sublingual or buccal dosage form to GSH levels from administration of an oral dosage form.

Example 5

In this example, a study evaluates sensory smell of formulations comprising N-acetylcysteine (NAC). The aim of this double-blind, randomized, sensory evaluation study was to evaluate the olfactory attributes of three formulations of NAC with naïve healthy adult assessors.

Study Formulations: The three NAC formulations (one control and two study formulations) are summarized in Table 1.

TABLE 1

| Code | Formulations |
|---|---|
| A (Control) | 20% NAC with 0.025% EDTA, adjusted to pH 7 with NaOH |
| B (Test) | 200 mg/mL NAC, 0.2M Sodium Ascorbate, pH 5.5, 0.02% BH 0.1% EDTA, 0.5% HPBCD, 1.0% Mannitol, 0.1% Menthol |
| C (Test) | 200 mg/mL NAC, 0.2M Sodium Ascorbate, pH 5.5, 0.02% BHT 0.1% EDTA, 0.5% HPBCD, 1.0% Mannitol, 0.1% Vanillin |

Ethylenediaminetetraacetic acid (EDTA) and Butylated Hydroxytoluene (BHT) are included as additional antioxidants to prevent NAC oxidation. Beta-cyclodextrin (HPBCD) is included as a masking agent to mask the smell of NAC. Mannitol is included as a sweetening agent. Formulation A served as a Control, and is essentially the same as the commercially available Mucomyst composition.

Samples were prepared on the day of the study by dispensing 10 mL of each liquid formulation into 15 mL amber glass bottles. The bottles were sealed with caps and labelled with codes for blinding. The closed sample bottles were allowed to stand for a minimum of two hours to facilitate buildup of the scent within the bottle.

Methodology: The study was conducted in a well-ventilated, odorless environment with ample daylight and free of noise and distraction to avoid any influence on sensory evaluation. Participants were seated at individual stations with responses collected using a computerized data collection form.

In part 1 of the study, participants completed the Q-SIT™ screening. The commercial Q-SIT™ was purchased from Sensonics International (New Jersey, USA). This part used individual cards containing three microencapsulated odorant strips. Participants were instructed to scratch each strip with their fingernail to release the odor and select the most appropriate descriptor based on a multiple-choice question with five options (e.g., banana, peanut, rose, paint thinner, none/other).

In part 2, participants evaluated the three NAC formulations sequentially in a randomized order. As illustrated in Table 2, six randomization sequences were generated based on the Williams design, a Latin square, high-crossover design to achieve balance and maximize comparisons with the fewest number of subjects.

TABLE 2

| Randomization sequence | Number of participants presented with sequence (%) |
|---|---|
| ABC | 7 (18%) |
| ACB | 7 (18%) |
| BAC | 7 (18%) |
| BCA | 7 (18%) |
| CAB | 6 (15%) |
| CBA | 6 (15%) |

Participants were instructed to unscrew the bottle cap, close their eyes, and smell the contents while concentrating on the odor, moving the bottle between the nostrils if needed. Participants then rated, ranked, and appraised the samples using the data collection form.

A mix of quantitative and qualitative measures was used to enable a more comprehensive understanding of the olfactory experiences. This mix included:

(1) Rating the smell pleasantness on a visual analogue scale (VAS) from 1 to 100. This provided a quantitative measure of hedonic response to the smell and participants' emotional reaction to it. The scale ranged from 1 as "extremely unpleasant" and 100 as "extremely pleasant" with a midpoint of 50 representing a neutral response. Corresponding graphics of facial expressions were illustrated in the scale.

(2) Rating the smell intensity on 5-point ordinal scale from very mild to very strong. This measured the perceived strength of the smell, independent of the hedonic rating (i.e. a sample might have a very strong scent but still be pleasant, or a mild scent might be unpleasant). Intensity ratings indicated how prominent or subtle the smell was, but not the emotional response to it.

(3) Ranking the three formulations in order of acceptability from 1-3. This involved ranking the three samples in terms of acceptability, with 1 being the most acceptable and 3 being the least acceptable after all three samples had been evaluated. This indicated the overall preference for each sample, considering both hedonic (pleasantness) and sensory (intensity) aspects.

(4) Open comments and feedback. This provided more
   detailed, subjective descriptions of the smell for each
   sample, to add further depth to the quantitative ratings
   and further insights into why the sample may have been
   liked or disliked.

In both parts of the study, a minimum 2-minute interval
was maintained between sample evaluations, as timed by the
researcher. During this time, participants were instructed to
drink water, sniff their forearm, and take deep breaths to
cleanse their nose between samples. Participants were asked
to confirm that they could no longer perceive any residual
smells each time before moving onto the next sample.

Subjects: healthy adults classified as "naïve assessors",
namely, those who do not have to meet any precise criterion
to perform the sensory tests.

Inclusion criteria for participation in the study included:
Female and male adults aged 18 to 40 years; Non-immu-
nocompromised and free from any health conditions or
chronic lung diseases, such as asthma; Non-smokers; Good
understanding of the English language; Able to provide
informed consent for participation in the study; Willing to
refrain from wearing perfume or scented products on the day
of the study, especially on the wrists, arms, or hands.

Exclusion criteria included: Smokers; Any sensory disor-
ders affecting smell; Any drug allergies; Pregnancy or
breastfeeding; Any dental care or medicinal treatment up to
15 days before study; Any coughs, colds or symptoms of
COVID-19 72 hours before the study.

Ethical Considerations: The study was approved by the
institutional research ethics committee. Participants
reviewed a comprehensive study information sheet and
provided informed consent via a signed online form prior to
participation. Participation was voluntary, and participants
were free to withdraw at any time without penalty or the
obligation to provide a reason.

All data was collected and stored securely in encrypted
format within the data collection software. Each participant
was assigned a pseudo-anonymized participant code, and
aside from their sensory ratings, participants reported their
age and sex as study data. As part of the ethics approval, the
study was registered with an institutional data protection
office. All data was collected and processed in accordance
with applicable laws and regulations.

Data Analysis: For the Q-SIT™ screening, a total score
from 0-3 was calculated for each participant based on each
correct response for the odor descriptors. For the sensory
evaluation of the NAC formulations, a mixed model (or
mixed error-component model) was used to analyze the VAS
ratings for smell pleasantness. This statistical model sets
both fixed effects and random effects in the same analysis to
account for results from repeated measures. Fixed effects
included the sample formulation (A-C) and the period when
the sample was evaluated based on randomization order (i.e.
as the 1st-3rd sample). Individual participant codes were set
as the random effect. Differences in sample ratings deemed
to be statistically significant (p<0.05) were analyzed as
pairwise comparisons. Analysis was completed using R
open-source software (version 4.3.1 (2023 Jun. 16)). The
intensity ratings, rank order preference, and qualitative
comments were analyzed and compared descriptively.

Q-SIT™ Screening Results: Overall, 85% (34/40) of
participants scored a total of 3 and 15% (6/40) scored 2 in
the Q-SIT™ screening. In the published research study
evaluating tool (Jackman and Doty, 2005), among normos-
mic participants (i.e. those with a normal sense of smell)
62.5% scored 3, 25% scored 2, 12.5% scored 1, and none
scored 0. Based on these findings, all participants passed the screening, and their corresponding data was included in the
overall analysis of the NAC formulations.

Smell Pleasantness Results: Table 3 shows the summary
statistics for the hedonic pleasantness ratings, and the box-
plots in FIG. 1 depicts the distribution and variability of
these ratings.

TABLE 3

|  | A | B | C |
|---|---|---|---|
| Mean ± SD | 23.7 ± 16.3 | 50.4 ± 26.2 | 27.9 ± 20.1 |
| Median (IQR) | 19.5 (14.8, 35.2) | 56.0 (30.0, 66.0) | 27.0 (11.8, 36.2) |
| Range | 1-67 | 1-100 | 1-100 |

In FIG. 1, Boxplots illustrating the VAS ratings for smell
pleasantness from 1 "Extremely Unpleasant" to 50 "Neu-
tral" to 100 "Extremely Pleasant". Data are visualized as
notched boxplots consisting of a central line indicating the
median, the box indicative of the interquartile range and the
whiskers being 1.5 times the 25th and 75th percentile,
respectively. Dots represent ratings for individual partici-
pants. The notches are indicative of the 95% confidence
interval of the median, such that if the notches of respective
boxes do not overlap, there is strong evidence that their
medians differ significantly.

Overall, 62.5% (25/40) rated formulation B as pleasant
(>50 on the VAS). In comparison, only 10% (4/40) of
participants rated both formulations A and C as pleasant. The
results of the mixed model statistical analysis showed that
formulation B had a significantly higher smell pleasantness
rating than formulations A or C (p<0.0001). There was no
significant difference between formulations A and C
(p=0.319). The complete outputs of the mixed model analy-
sis are included in the appendix.

Figure 2:
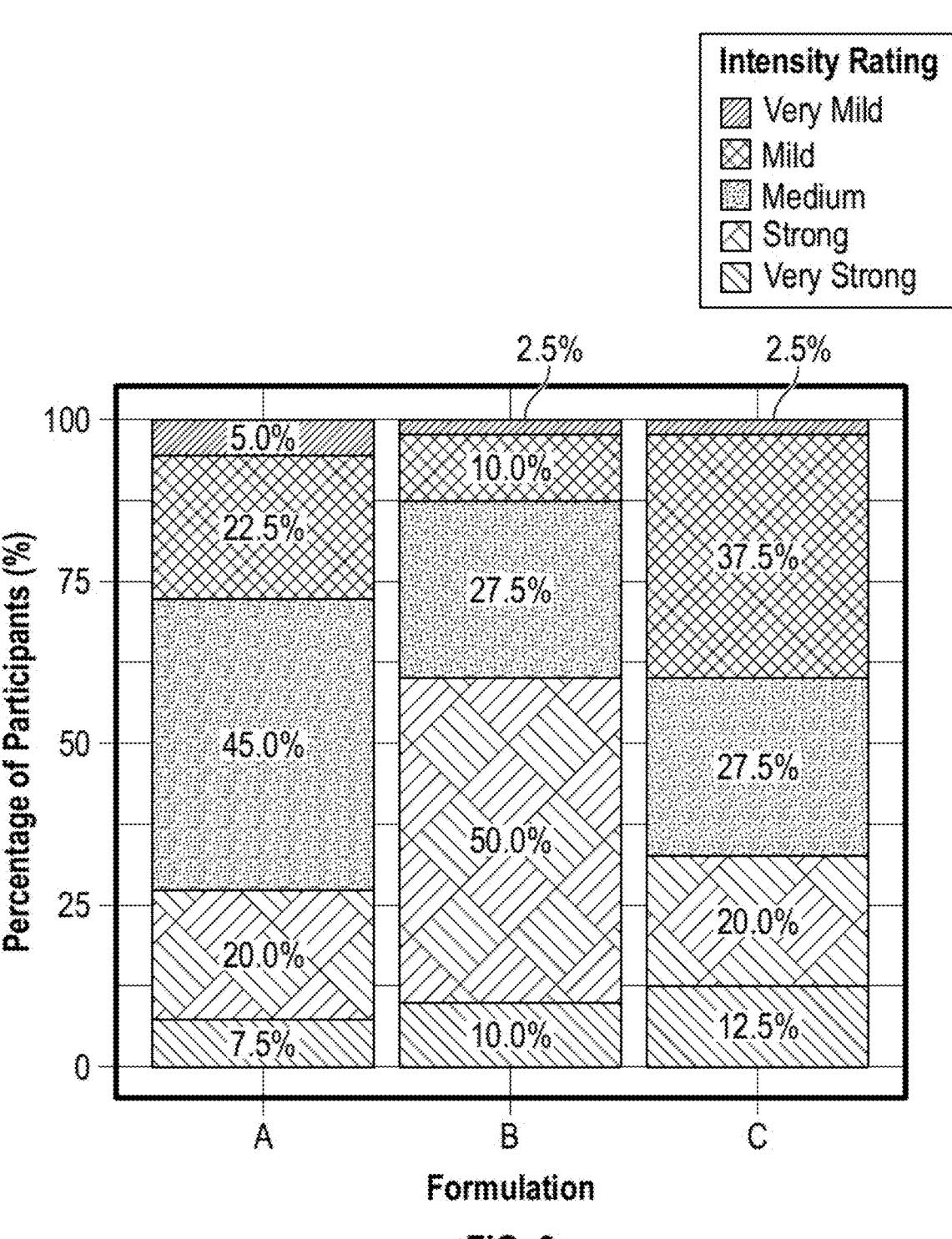
FIG. 2 shows smell intensity results from the sensory smell study of Example 5.

Smell Intensity Results: FIG. 2 shows the smell intensity
ratings on 5-point ordinal scale from very mild to very
strong for the three formulations. For formulation B, 60% of
participants rated the scent as "strong" or "very strong,"
compared to 27.5% for formulation A and 32.5% for for-
mulation C. However, these intensity ratings were not nec-
essarily correlated with the hedonic evaluation of the smell,
but mainly to the presence of the perceivable menthol scent
in this formulation.

For formulation B, the intensity ratings between partici-
pants who found the scent pleasant (>50 on the VAS; n=25)
versus those who found it unpleasant (<50 on the VAS;
n=15) was comparable: 8% vs. 13% for very strong; 48% vs.
53% for strong; 32% vs. 20% for medium; 8% vs. 13% for
mild; and 4% vs. 0% for very mild. A similar comparison
was not completed for formulations A and C due to the
limited number of participants who rated these formulations
as pleasant.

Figure 3:
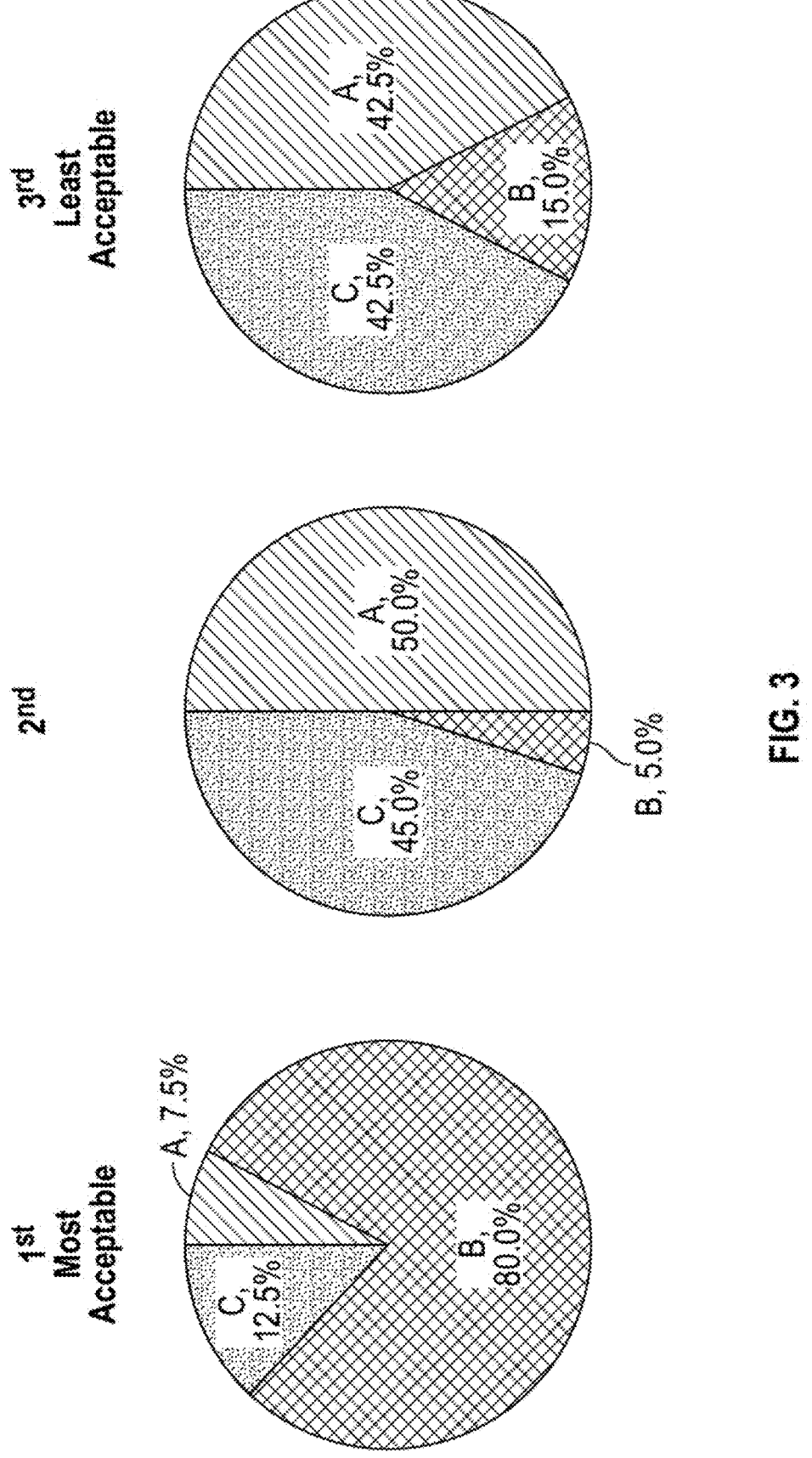
FIG. 3 shows ranked preferences for the formulations in the sensory smell study of Example 5.

Rank Preference Results: As shown in FIG. 3, 80% of
participants ranked formulation B as the most acceptable of
the three NAC formulations. Formulations A and C were
equally ranked as the least acceptable formulations by
42.5% of participants, respectively.

Open Comments Results: The comments from partici-
pants revealed a range of sensory responses to the three
formulations, with notable differences in the perception of
pleasantness and specific scent descriptors. Formulation B
was often described in more positive terms than A and C.
Numerous participants perceived menthol aroma in the
sample and described it positively e.g. "minty", "menthol",
"peppermint", "Vicks-like", and "eucalyptus". Positive
hedonic descriptors such as "pleasant" "refreshing" "soothing", "fresh" and "acceptable" were also used to describe the sample. Two participants (15 and 17) described the sample more negatively (e.g. reminiscent of "Chinese traditional medicine", "nail polish remover", or "herbal"), while four participants mentioned that the menthol odor could be too intense or overwhelming.

Although the menthol odor was prominent, many participants also noted that the unpleasant odor of NAC was still perceptible in the sample e.g. participant 13: "the unpleasant smell still slightly occurs"; participant 17: "with a hint of rotten eggs"; participant 18: "hints of mint/menthol but it did not mask the unpleasant smell"; and participant 19: "a hint of a bad smell there". As such, formulation B was often found to be comparatively better than A and C e.g. participant 30: "all 3 samples are kind of unacceptable. But the sample 694 is the least unacceptable" and participant 10 "overall none of them smells that good, but 694 was definitely better and much more pleasant".

Formulations A and C were predominantly described in negative terms, with several participants using descriptors such as "rotten eggs", "methane", "sulfur", "ammonia", "sewage", "toilet" and "fart" to describe the smell of the samples. Other descriptors included "similar to mixed spices such as asafetida", "fishy" and like "burnt hair". Negative hedonic descriptors included "horrible", "disgusting", "unpleasant", "offensive", and nauseating. Formulation C was described by some participants as slightly less unpleasant than A in terms of intensity (e.g., "milder," "less strong," "more acceptable"), but still generally unpleasant.

Conclusions: This sensory evaluation study assessed the olfactory properties of three NAC formulations with 40 healthy adult participants who evaluated the smell pleasantness, intensity, and overall preference using both quantitative and qualitative measures. The results revealed significant differences in the sensory profiles of the three formulations, with formulation B emerging as the most pleasant and highest ranked. Formulations A and C were consistently rated more negatively. Formulation B, with its perceptible menthol scent, shows strong potential as a more acceptable product, though further refinements may be necessary to fully mask the undesirable odor of NAC which was still perceptible to some degree, despite the reduced intensity reported by participants in open comments.

The study underscores the importance of odor masking strategies when developing non-parenteral NAC formulations, particularly given the strong aversion that participants expressed toward the characteristic sulfurous odor of NAC. For products administered orally or intranasally, both orthonasal and retronasal olfaction have an important impact, as these are distinct pathways through which odors are perceived by the human olfactory system. Orthonasal olfaction occurs when odors are inhaled directly through the nostrils, while retronasal olfaction is perceived when odors are released from the mouth into the nasal cavity during exhalation or swallowing (often influencing taste experiences).

Example 6

In this example, a study was conducted to assess the taste characteristics of a test formulation comprising N-acetyl-cysteine (NAC) in comparison to a conventional NAC formulation. The study was conducted with the "E-Tongue" test of Medallion Labs of Minneapolis, MN. The E-tongue test uses taste sensors to detect dissolved organic and inorganic compounds. Like human receptors, each sensor has a spectrum of reactions different from the other. The information given by each sensor is complementary and sent to a pattern recognition system, and the combination of the sensors' results generates a taste profile. The result is the detection of the tastes that compose the human palate.

In this study, a scale of 1.0 units was determined to be differential sensitivity which estimates to 20% difference in taste. Table 4 shows the sensors used in the study and corresponding tastes. Sweetness was not analyzed in this study.

TABLE 4

| Sensor name | Corresponding taste | Taste information | |
|---|---|---|---|
| | | Initial Taste | After Taste |
| AAE | Umami | Umami | Richness |
| CT0 | Saltiness | Saltiness | X |
| CA0 | Sourness | Sourness | X |
| C00 | Acidic Bitterness | Bitterness | Aftertaste-B (Aftertaste of Bitterness) |
| AE1 | Astringency | Astringency | Aftertaste-A (Aftertaste of Astringency) |

The comparator and test formulation used for this study are set forth in Table 5.

TABLE 5

| Formulations | |
|---|---|
| Comparator | Control: 20% NAC with 0.025% EDTA, adjusted to pH 7 with NaOH |
| Test | Formulation_003: 200 mg/mL NAC, 0.2M Sodium Ascorbate, pH 5.5, 0.02% BHT 0.1% EDTA, 0.5% HPBCD, 1.0% Mannitol, 0.1% Vanillin |

Figure 4A:
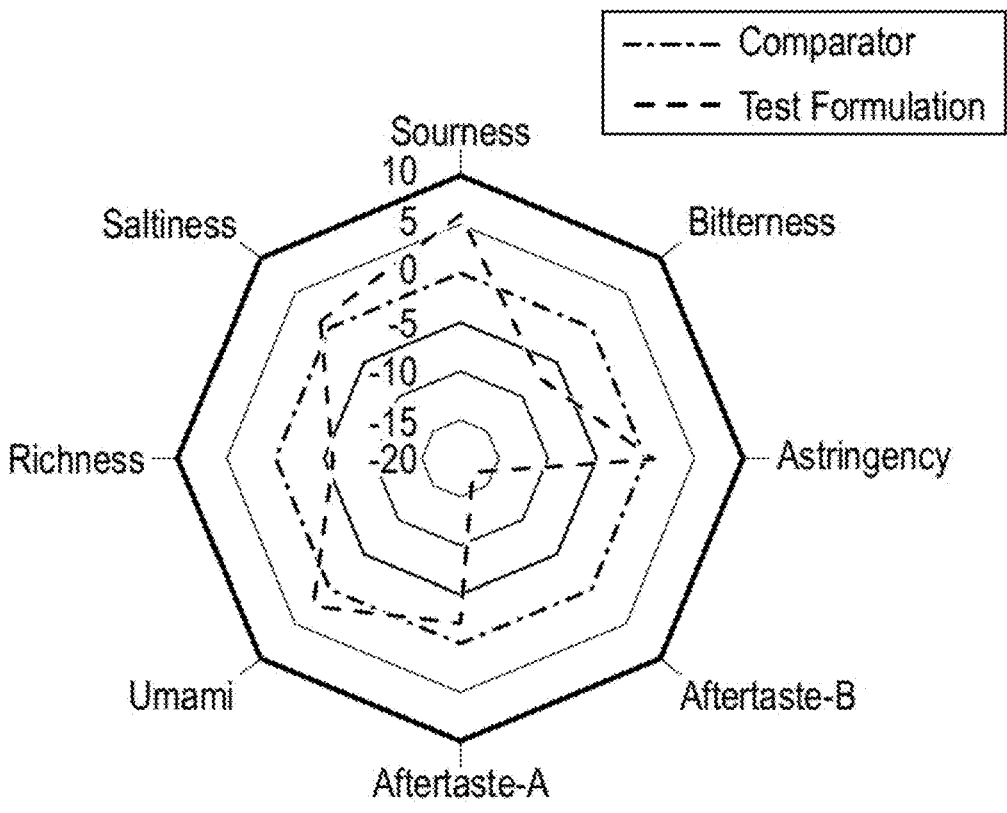
FIGS. 4A to 4C show taste profiles from the taste study described in Example 6.
Figure 4B:
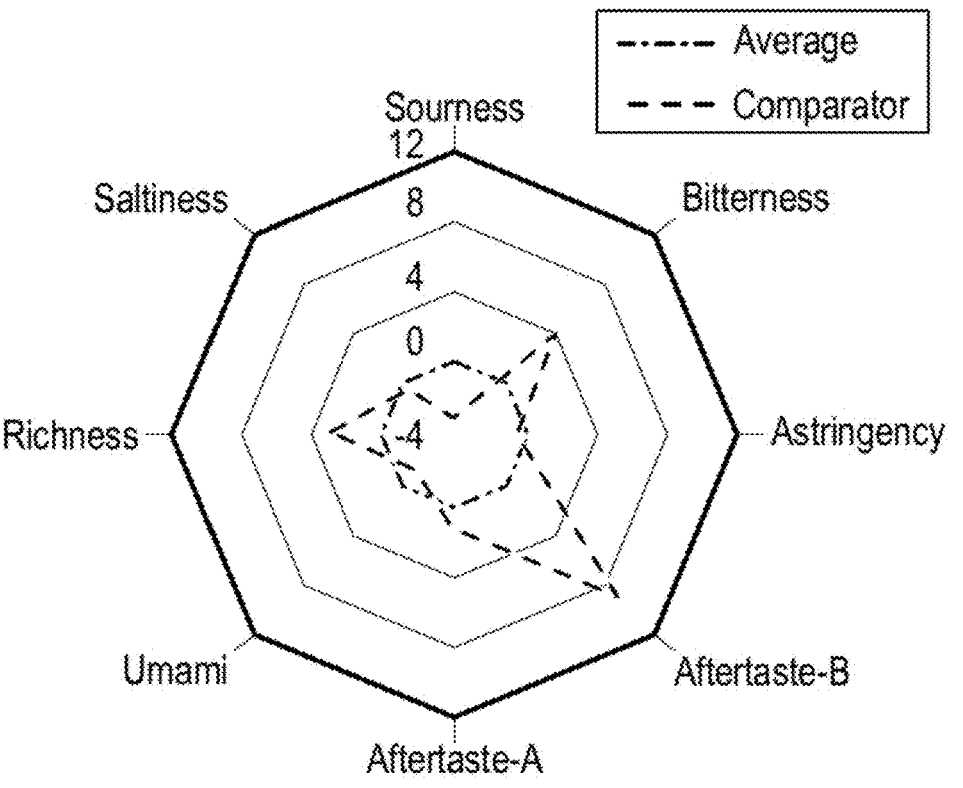
Figure 4C:
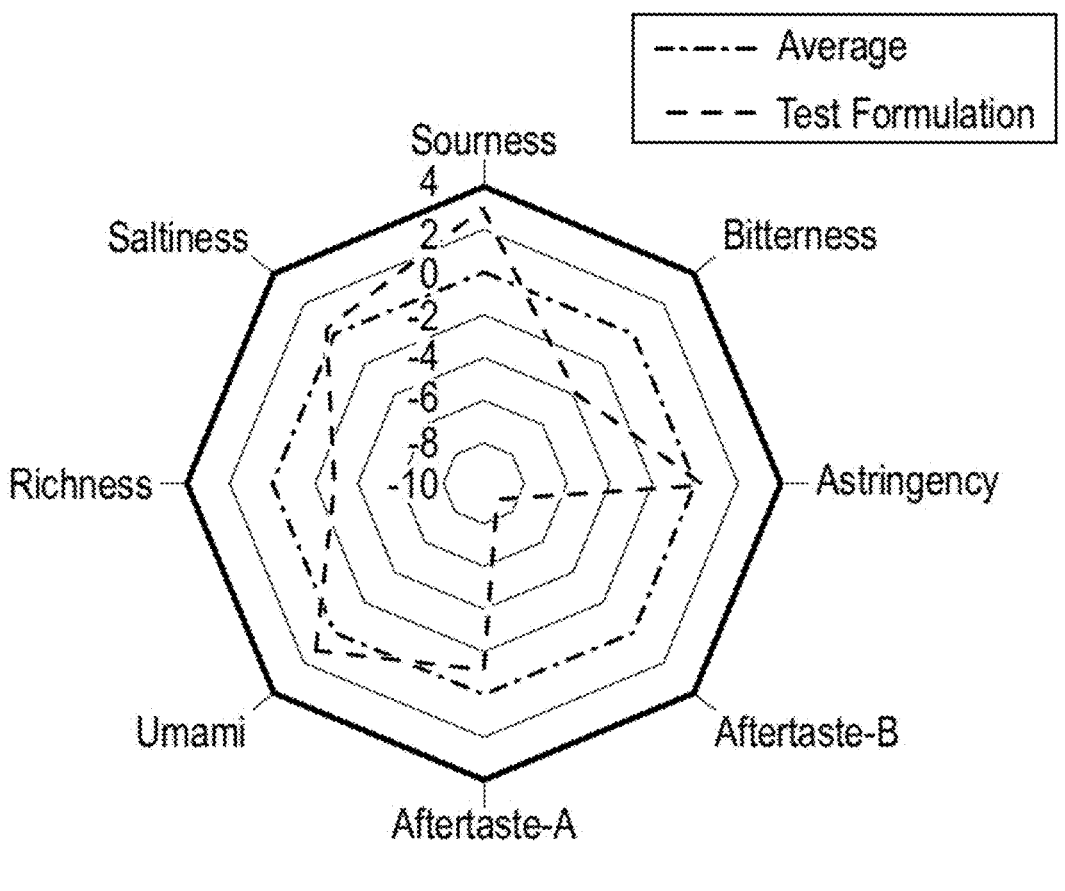

The results from this study are illustrated in FIGS. 4A to 4C and in Table 6. FIG. 4A shows a taste profile in which the comparator formulation is zero, and the relative tastes of the test formulation are shown. FIGS. 4B and 4C show the taste comparison for the comparator and the test formulation, respectively, based on the difference to the average of all samples in the study.

TABLE 6

| | Comparator | Test |
|---|---|---|
| Sourness | 0 | 6.03 |
| Bitterness | 0 | −7.78 |
| Astringency | 0 | 0.7 |
| Aftertaste-B | 0 | −17.93 |
| Aftertaste-A | 0 | −2.54 |
| Umami | 0 | 2.17 |
| Richness | 0 | −5.91 |
| Saltiness | 0 | 0.9 |

The results of this study demonstrate that the test NAC formulation was reduced in Bitterness and Aftertaste-B (Bitter) to a great extent. These results indicate that agents such as HPBCD and mannitol were highly effective in reducing Bitterness and Bitter Aftertaste from NAC.

Example 7

In this study, the effect of taste of a sublingual or buccal dosage form on its pharmacokinetics is evaluated. A dosage form comprising NAC and an effective amount of one or more masking agents (such as a bitter-blocker and/or a sweetening agent) is administered to a subject. The sublingual or buccal dosage form comprising the effective amount of one or more masking agents is to be retained in the mouth for as long as possible. The length of time in which the subject retains the dosage form in her mouth is measured. One or more measurements of the subject's blood level of NAC are made, such as peak blood level and/or time to peak blood level and/or area under the curve (AUC) over 1, 2, 12, or 24 hours. The blood level is compared to measurements from the same or different subjects who are administered a sublingual or buccal dosage form without a masking agent, and/or with a different masking agent, and/or with a different amount of a masking agent. Alternatively, the blood level measurement is compared to blood levels of NAC from a swallowed dosage form such as a pill.

The sublingual or buccal dosage form comprising NAC and an effective amount of one or more masking agents (such as a bitter-blocker and/or a sweetening agent) is retained by the subject in her mouth for a longer period of time and produces better pharmacokinetic properties, including one or more of a higher peak blood level, a shorter time to peak blood level, and/or a greater area AUC.

EXEMPLARY EMBODIMENTS

Exemplary embodiments provided in accordance with the presently disclosed subject matter include, but are not limited to, the claims and the following embodiments:

A. A method of treating a central nervous system (CNS) disorder, the method comprising sublingually or buccally administering to a subject an effective amount of at least one antioxidant compound or a pharmaceutically acceptable salt thereof.

A1. The method of embodiment A, wherein the antioxidant compound is selected from the group consisting of N-acetylcysteine (NAC), glutathione, co-enzyme Q-10, superoxide dismutase (SOD), and a combination thereof.

A2. The method of embodiment A or A1, wherein the method further comprises administering to the subject trofinetide, progesterone, neurosteroid, a ghrelin compound, a salt thereof, or a combination thereof.

A3. The method of any of embodiments A to A2, wherein the central nervous system disorder is selected from traumatic brain injury (TBI), post-concussive syndrome, Parkinson's disease, Huntington's disease, Alzheimer's disease, stroke, depression, bipolar disorder, multiple sclerosis (MS) and amyotrophic lateral sclerosis (ALS).

A4. The method of any of embodiments A to A2, wherein the central nervous system disorder is addiction such as but not limited to drug, alcohol, gambling and sex addiction.

A5. The method of any of embodiments A to A2, wherein the CNS disorder is nerve agent exposure, alphaviruses, seizures and coronaviruses.

A6. The method of any of embodiments A to A2, wherein the subject is CNS disorder is from exposure to a chemical warfare agent selected from the group consisting of nerve agents (including organophosphates; G-agents such as sarin, cyclosarin, tabun, and soman; and V-agents such as VE, VG, VM, VR, and VX); blistering agents such as nitrogen mustard, sulfur mustard or other mustard gas; asphyxiants such as carbon monoxide, chlorine, phosgene, and hydrogen sulfide gases; blood agents such as cyanide; and hydrofluoric acid.

A7. The method of any of embodiments A or A2, wherein the subject is in need of treatment for infection with a neurotropic virus.

A8. The method of embodiments A to A2, wherein the subject is in need of treatment for infection with an alphavirus.

A9. The method of any of embodiments A to A2, wherein the virus is a naturally occurring virus.

A10. The method of any of embodiments A to A2, wherein the virus is a genetically modified virus or a weaponized virus.

A11. The method of any of embodiments A to A10, wherein the method further comprises administering to the subject an inhibitor of an purinergic receptor selected from the group consisting of P2X4, P2X7, P2Y6, and P2Y12.

A12. The method of any of embodiments A to A11, wherein the at least one antioxidant is administered in combination with a chitosan loaded nanoparticle, a lipophilic micelle, or a liposomal carrier.

A13. The method of any of embodiments A to A12, wherein the sublingual or buccal dosage form comprises one or more sweetening agents or flavoring agents.

A14. The method of any of embodiments A to A13, wherein the sublingual or buccal dosage form comprises one or more additives that prevents or slows oxidation of the at least one antioxidant compound or salt thereof.

A15. The method of any of embodiments A to A14, wherein the sublingual or buccal dosage form comprises one or more masking agents that alleviate odor or taste of the antioxidant compound.

A16. The method of embodiment A15, wherein the one or more masking agents reduces bitter taste.

A17. The method of embodiment A15, wherein the one or more masking agents comprises a bitter-blocker.

A18. The method of any of embodiments A15 to A17, wherein the one or more masking agents comprises menthol.

A19. The method of any of embodiments A to A18, wherein the at least one antioxidant compound or salt thereof is administered from 1 to 90 days or from 1 to 30 days for an acute disorder, or for an indefinite period for a chronic disorder.

A20. The method of any of embodiments A to A19, wherein the subject is a human.

A21. The method of any of embodiment A to A20, wherein the sublingual or buccal dosage form is any of embodiments C to C36.

B. A method of treating a central nervous system (CNS) disorder, the method comprising sublingually or buccally administering to a human subject an effective amount of at least one antioxidant compound or a pharmaceutically acceptable salt thereof, wherein the method comprises administering a total daily dose of the antioxidant compound or salt thereof from about 0.001 to about 100 mg/kg.

B1. The method of embodiment B, wherein the antioxidant compound is selected from the group consisting of N-acetylcysteine (NAC), glutathione, co-enzyme Q-10, superoxide dismutase (SOD), and a combination thereof.

B2. The method of embodiment B or B1, wherein the method further comprises administering to the subject a non-steroid anti-inflammatory agent.

B3. The method of any of embodiments B to B2, wherein the method further comprises administering to the subject trofinetide, progesterone, neurosteroid, a ghrelin compound, a salt thereof, or a combination thereof.

B4. The method of any of embodiments B to B3, wherein the central nervous system disorder is selected from traumatic brain injury (TBI), concussion, post-concussion syndrome, Parkinson's disease, Huntington's disease, stroke, depression, bi-polar disorder, Alzheimer's disease, multiple sclerosis (MS) and amyotrophic lateral sclerosis (ALS).

B5. The method of any embodiments B to B4, wherein the central nervous system disorder or damage is caused by nerve agent exposure, alphaviruses, seizures and coronaviruses.

B6 The method of any embodiments B to B5, wherein the central nervous system is effected by addictions such as drug, alcohol, gambling or sex addictions.

B7. The method of any of embodiments B to B6, wherein the method further comprises administering to the subject an agent for enhancing delivery of and/or alleviating odor or taste from the at least one antioxidant compound or salt thereof.

B8. The method of embodiment B7, wherein the agent comprises a cyclodextrin compound in an amount effective to enhance delivery of and/or alleviate odor from the at least one antioxidant compound or salt thereof.

B9. The method of embodiment B8, wherein the agent comprises (2-hydroxypropyl) beta-cyclodextrin (HPBCD).

B10. The method of any of embodiments B to B9, wherein the at least one antioxidant compound or salt thereof is administered as a pharmaceutical formulation comprising the at least one antioxidant in combination with one or more sweetening or flavoring agents.

B11. The method of any of embodiments B to B10, wherein the at least one antioxidant compound or salt thereof is administered from 1 to 30 days.

B12. The method of any embodiments B to B11, wherein the at least one antioxidant compound or salt thereof is administered indefinitely, until death or the disease is cured.

C. A sublingual or buccal dosage form comprising at least one antioxidant compound or pharmaceutically salt thereof.

C1. The sublingual or buccal dosage form of embodiment C, wherein the at least one antioxidant compound or salt thereof is the only active agent in the dosage form.

C2. The sublingual or buccal dosage form of any of embodiments C to C1, wherein the at least one antioxidant compound is selected from the group consisting of N-acetylcysteine (NAC), glutathione, co-enzyme Q-10, superoxide dismutase (SOD), and a combination thereof.

C3. The sublingual or buccal dosage form of any of embodiments C to C1, wherein the at least one antioxidant compound is N-acetylcysteine (NAC).

C4. The sublingual or buccal dosage form of any of embodiments C to C3, comprising up to 120 mg of the at least one antioxidant compound.

C5. The sublingual or buccal dosage form of any of embodiments C to C3, comprising from about 30 to about 90 mg of the at least one antioxidant compound.

C6. The sublingual or buccal dosage form of any of embodiments C to C5, wherein the at least one antioxidant compound or pharmaceutically salt thereof is deoxygenated.

C7. The sublingual or buccal dosage form of any of embodiments C to C6, further comprising a water-soluble polymer.

C8. The sublingual or buccal dosage form of embodiment C7, wherein the water-soluble polymer is selected from the group consisting of HPMC E3, E5 and E15 and K-3, Methyl cellulose A-3, A-6 and A-15, Pullulan, carboxymethylcellulose cekol 30, polyvinylpyrrolidone PVP K-90, pectin, gelatin, sodium, alginate, hydroxypropyl cellulose, polyvinyl alcohol, maltodextrins, and combinations thereof.

C9. The sublingual or buccal dosage form of any of embodiments C to C8, further comprising a plasticizer.

C10. The sublingual or buccal dosage form of embodiment C9, wherein the plasticizer is selected from the group consisting of glycerol, dibutyl phthalate, polyethylene glycol, and combinations thereof.

C11. The sublingual or buccal dosage form of any of embodiments C to C10, further comprising a sweetening agent.

C12. The sublingual or buccal dosage form of embodiment C11, wherein the sweetening agent is selected from saccharin, cyclamate, aspartame, and combinations thereof.

C13. The sublingual or buccal dosage form of embodiment C11, wherein the sweetening agent is from mannitol, sucrose, saccharin, cyclamate, aspartame, and combinations thereof.

C14. The sublingual or buccal dosage form of any of embodiments C to C13, further comprising a saliva stimulating agent.

C15. The sublingual or buccal dosage form of embodiment C14, wherein the saliva stimulating agent is selected from the group consisting of citric acid, malic acid, lactic acid, ascorbic acid, or a salt thereof, and combinations thereof.

C16. The sublingual or buccal dosage form of any of embodiments C to C15, further comprising one or more surfactants.

C17. The sublingual or buccal dosage form of embodiment C16, wherein the one or more surfactants is selected from the group consisting of sodium lauryl sulfate, benzalkonium chloride, Tween, and combinations thereof.

C18. The sublingual or buccal dosage form of any of embodiments C or C17, further comprising one or more fillers.

C19. The sublingual or buccal dosage form of any of embodiments C to C18, further comprising one or more coloring agents.

C20. The sublingual or buccal dosage form of any of embodiments C to C19, further comprising one or more flavoring agents.

C21. The sublingual or buccal dosage form of any of embodiments C to C20, further comprising one or more masking agents.

C22. The sublingual or buccal dosage form of embodiment C21, wherein the one or more masking agents alleviates odor or taste.

C23. The sublingual or buccal dosage form of embodiment C22, wherein the one or more masking agents alleviates bitter taste and/or an aftertaste of bitterness.

C24. The sublingual or buccal dosage form of embodiment C23, wherein the one or more masking agents is present in an amount having an acceptable smell intensity.

C25. The sublingual or buccal dosage form of any of embodiments C to C24, wherein the dosage form is a dissolving strip.

C26. The sublingual or buccal dosage form of any of embodiments C to C25, wherein the dosage form is a lozenge.

C26. The sublingual or buccal dosage form of any of embodiments C to C25, wherein the dosage form is a lollypop.

C27. The sublingual or buccal dosage form of any of embodiments C to C25, wherein the dosage form is a chewing gum.

C28. The sublingual or buccal dosage form of any of embodiments C to C27, wherein the dosage form comprises NAC in an amount from 20 to 2000 mg/mL, alternatively 200 mg/mL.

C29. The sublingual or buccal dosage form of any of embodiments C to C28, wherein the dosage form comprises sodium ascorbate in an amount from 0.02M to 2M, alternatively 0.2M.

C30. The sublingual or buccal dosage form of any of embodiments C to C29, wherein the dosage form comprises BHT in an amount from 0.002% to 0.2%, alternatively 0.02%, by weight.

C31. The sublingual or buccal dosage form of any of embodiments C to C30, wherein the dosage form comprises EDTA in an amount from 0.01% to 1%, alternatively 0.1%, by weight.

C32. The sublingual or buccal dosage form of any of embodiments C to C31, wherein the dosage form comprises β-CD in an amount from 0.05% to 5%, alternatively 0.5%, by weight.

C33. The sublingual or buccal dosage form of any of embodiments C to C32, wherein the dosage form comprises mannitol in an amount from 0.1% to 10%, alternatively 1%, by weight.

C34. The sublingual or buccal dosage form of any of embodiments C to C33, wherein the dosage form comprises menthol in an amount from 0.01% to 1%, alternatively 0.1%, by weight.

C35. The sublingual or buccal dosage form of any of embodiments C to C34, wherein the dosage form comprises 200 mg/mL NAC, 0.2M Sodium Ascorbate, 0.02% BHT 0.1% EDTA, 0.5% β-CD, 1% Mannitol, and 0.1% Menthol C36. The sublingual or buccal dosage form of any of embodiments C to C35, wherein the dosage form has a pH from 5 to 7, alternatively a pH of about 5.5.

D. A kit for treating a subject having a central nervous system (CNS) disorder, the kit comprising (a) a sublingual or buccal dosage form comprising a first antioxidant compound or a pharmaceutically acceptable salt thereof, and (b) an intranasal dose form comprising a second antioxidant compound or a pharmaceutically acceptable salt thereof.

D1. The kit of embodiment D, wherein the first and second antioxidant compounds are the same.

D2. The kit of any of embodiments D or D1, wherein the first and second antioxidant compounds are different.

D3. The kit of any of embodiments D or D2, wherein the kit further comprises instructions for using the components of the kit.

D4. The kit of any of embodiments D or D3, wherein the sublingual or buccal dosage form is any of embodiments C to C36.

The invention claimed is:

1. A sublingual or buccal dosage form comprising:
N-acetylcysteine (NAC) or pharmaceutically salt thereof;
one or more water-soluble polymers or plasticizers; and
one or more masking agents effective to alleviate odor or taste of NAC, wherein said one or more masking agents is present in an amount from 0.05% to 5% by weight.

2. The sublingual or buccal dosage form of claim 1, wherein the dosage form comprises NAC in an amount from 20 to 2000 mg/mL.

3. The sublingual or buccal dosage form of claim 1, wherein the dosage form comprises NAC in an amount up to 120 mg of NAC.

4. The sublingual or buccal dosage form of claim 1, wherein the one or more masking agents is present in an amount that alleviates bitter taste and/or an aftertaste of bitterness.

5. The sublingual or buccal dosage form of claim 1, wherein the one or more masking agents further comprises menthol.

6. The sublingual or buccal dosage form of claim 5, wherein the menthol is present in an amount from 0.01% to 1% by weight.

7. The sublingual or buccal dosage form of claim 1, wherein the dosage form comprises at least one water-soluble polymer, and the at least one water-soluble polymer comprises hydroxypropyl methylcellulose (HPMC) E3, HPMC E5, HPMC E15, HPMC K-3, Methyl cellulose A-3, Methyl cellulose A-6, Methyl cellulose A-15, Pullulan, carboxymethylcellulose, polyvinylpyrrolidone (PVP) K-90, pectin, gelatin, sodium, alginate, hydroxypropyl cellulose, polyvinyl alcohol, maltodextrins, or a combination thereof.

8. The sublingual or buccal dosage form of claim 1, wherein the dosage form comprises at least one plasticizer, and the at least one plasticizer comprises glycerol, dibutyl phthalate, polyethylene glycol, or a combination thereof.

9. The sublingual or buccal dosage form of claim 1, further comprising a sweetening agent.

10. The sublingual or buccal dosage form of claim 9, wherein the sweetening agent comprises mannitol, maltitol, sorbitol, sucrose, sucralose, dextrose, saccharin, cyclamate, aspartame, or a combination thereof.

11. The sublingual or buccal dosage form of claim 1, further comprising a saliva stimulating agent, or a salt thereof, comprising citric acid, malic acid, lactic acid, ascorbic acid, or a combination thereof.

12. The sublingual or buccal dosage form of claim 11, wherein the dosage form comprises sodium ascorbate in an amount from 0.02M to 2M.

13. The sublingual or buccal dosage form of claim 1, wherein the dosage form is a dissolving strip, lozenge, lollypop, or chewing gum.

14. The sublingual or buccal dosage form of claim 1, wherein the dosage form comprises butylated hydroxytoluene (BHT) in an amount from 0.002% to 0.2% by weight.

15. The sublingual or buccal dosage form of claim 1, wherein the dosage form comprises ethylenediaminetetraacetic acid (EDTA) in an amount from 0.01% to 1% by weight.

16. The sublingual or buccal dosage form of claim 1, wherein the dosage form comprises 200 mg/mL NAC, 0.2M sodium ascorbate, 0.02% BHT, 0.1% EDTA, 0.5% HPBCD, 1% mannitol, and 0.1% menthol.

17. A sublingual or buccal dosage form comprising:
N-acetylcysteine (NAC) or pharmaceutically salt thereof;
one or more water-soluble polymers or plasticizers; and
one or more masking agents effective to alleviate odor or
    taste of NAC, wherein said one or more masking agents
    comprises (2-hydroxypropyl) beta-cyclodextrin
    (HPBCD) present in an amount from 0.05% to 5% by
    weight.

18. The sublingual or buccal dosage form of claim 17,
wherein the dosage form comprises (2-hydroxypropyl) beta-
cyclodextrin (HPBCD) present in an amount from 0.1% to
1% by weight.

19. The sublingual or buccal dosage form of claim 17,
wherein the dosage form comprises (2-hydroxypropyl) beta-
cyclodextrin (HPBCD) present in an amount of about 0.5%
by weight.

20. The sublingual or buccal dosage form of claim 9,
wherein the sweetening agent is selected from the group
consisting of mannitol, maltitol, sorbitol, sucrose, sucralose,
dextrose, saccharin, cyclamate, aspartame, and combina-
tions thereof.

\* \* \* \* \*